United States Patent [19]
Neftel et al.

[11] Patent Number: 5,827,262
[45] Date of Patent: Oct. 27, 1998

[54] SYRINGE DEVICE FOR MIXING TWO COMPOUNDS

[75] Inventors: Frëdëric Neftel, Lausanne, Switzerland; Bernard Bouvier, Eragny sur Oise, France

[73] Assignee: Debiotech S.A., Lausanne, Switzerland

[21] Appl. No.: 617,838

[22] PCT Filed: Sep. 7, 1994

[86] PCT No.: PCT/FR94/01053

§ 371 Date: Mar. 7, 1996

§ 102(e) Date: Mar. 7, 1996

[87] PCT Pub. No.: WO95/07066

PCT Pub. Date: Mar. 16, 1995

[30] Foreign Application Priority Data

| | | | |
|---|---|---|---|
| Sep. 7, 1993 | [FR] | France | 93 10593 |
| Oct. 15, 1993 | [FR] | France | 93 12271 |
| Nov. 16, 1993 | [FR] | France | 93 13627 |
| Dec. 24, 1993 | [FR] | France | 93 15639 |
| Jan. 26, 1994 | [FR] | France | 94 00828 |
| Mar. 11, 1994 | [FR] | France | 94 02844 |
| May 25, 1994 | [FR] | France | 94 06314 |

[51] Int. Cl.$^6$ ............................................. A61B 19/00
[52] U.S. Cl. .................. 604/414; 604/82; 604/86; 604/87; 604/88
[58] Field of Search ..................... 604/82, 86, 87, 604/88, 411, 414, 415

[56] References Cited

U.S. PATENT DOCUMENTS

| | | | |
|---|---|---|---|
| 3,336,924 | 8/1967 | Sarnoff | 128/272 |
| 4,031,895 | 6/1977 | Porter | 128/272.1 |
| 4,303,071 | 12/1981 | Smith | 128/272.3 |
| 4,516,967 | 5/1985 | Kopfer | 604/87 |
| 4,909,290 | 3/1990 | Coccia | 141/329 |
| 5,088,996 | 2/1992 | Kopfer et al. | 604/415 |
| 5,125,908 | 6/1992 | Cohen | 604/196 |
| 5,247,972 | 9/1993 | Tetreault | 141/27 |

FOREIGN PATENT DOCUMENTS

| | | | |
|---|---|---|---|
| 0 022 977 | 7/1980 | European Pat. Off. | A61M 5/32 |
| 1 913 926 | 9/1970 | Germany. | |
| 2 211 104 | 6/1989 | United Kingdom | A61M 5/00 |
| WO 93/02723 | 2/1993 | WIPO | A61M 5/00 |

OTHER PUBLICATIONS

Copy of the International Search Report for PCT/FR94/01053, filed Sep. 4, 1994.

*Primary Examiner*—Wynn Wood Coggins
*Assistant Examiner*—N. Kent Gring
*Attorney, Agent, or Firm*—Wolf, Greenfield & Sacks, P.C.

[57] ABSTRACT

A syringe device for mixing two compounds is provided. The syringe device includes a vial having an opening and a centrally perforable stopper. The syringe device also includes a guide tube for guiding the injection end of the syringe between a withdrawn or storage position and an inserted position. The guide tube includes a second end for receiving the injection end of the syringe, which also includes a seal between the body of the syringe and the guide tube.

52 Claims, 16 Drawing Sheets

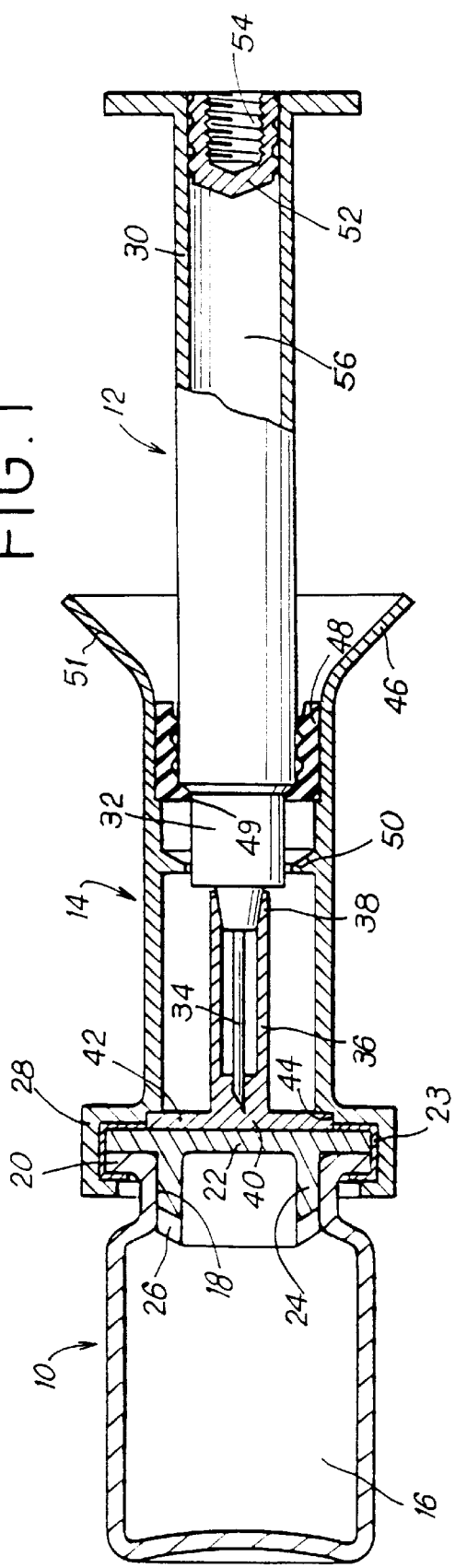
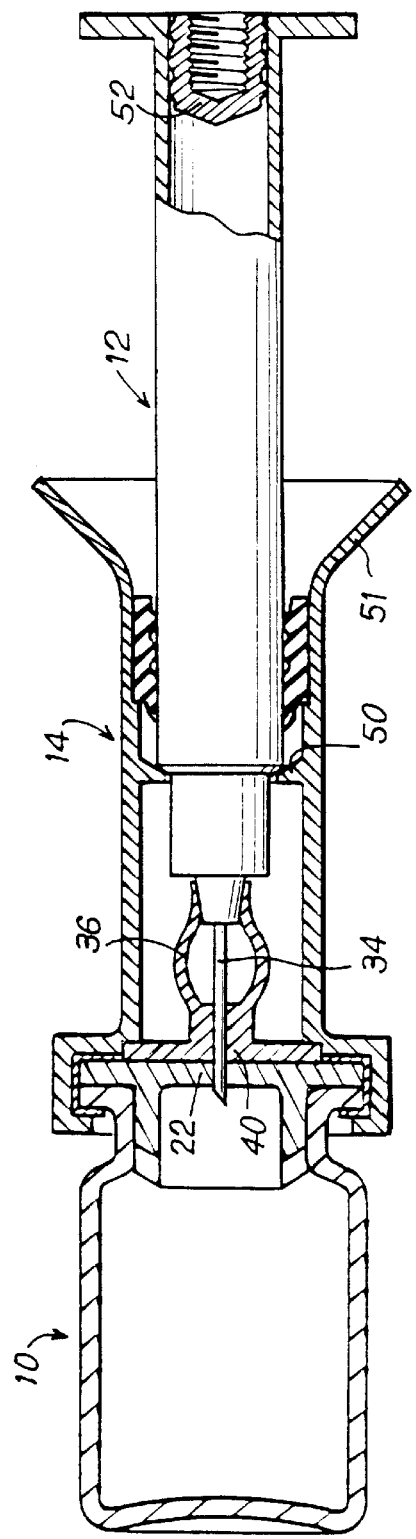

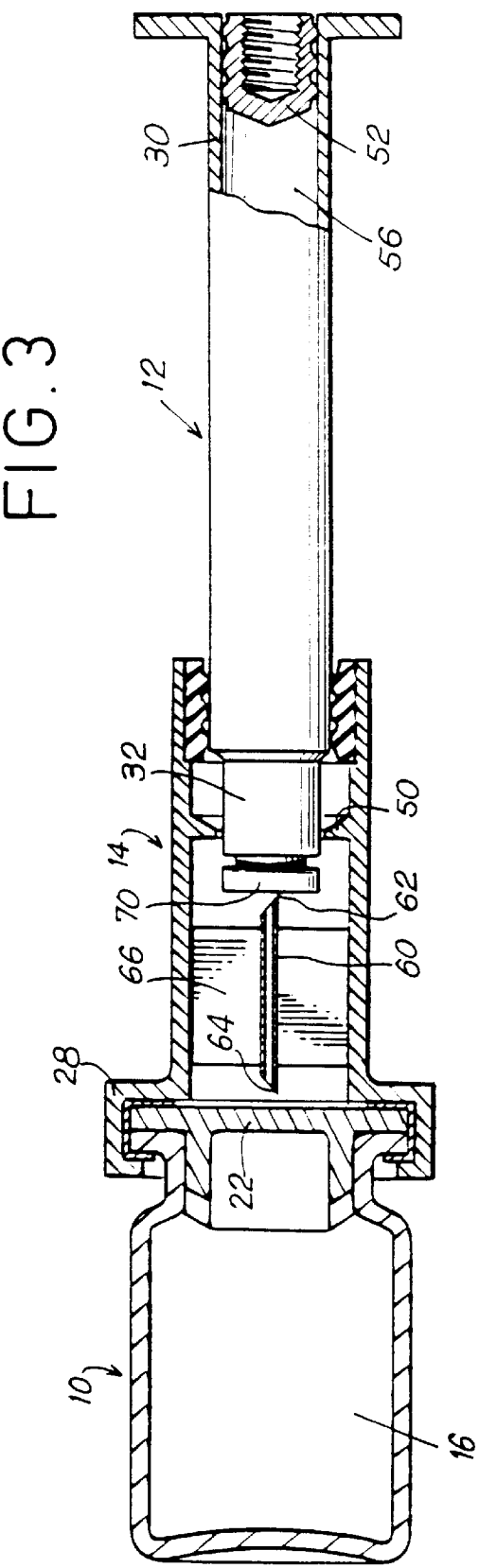
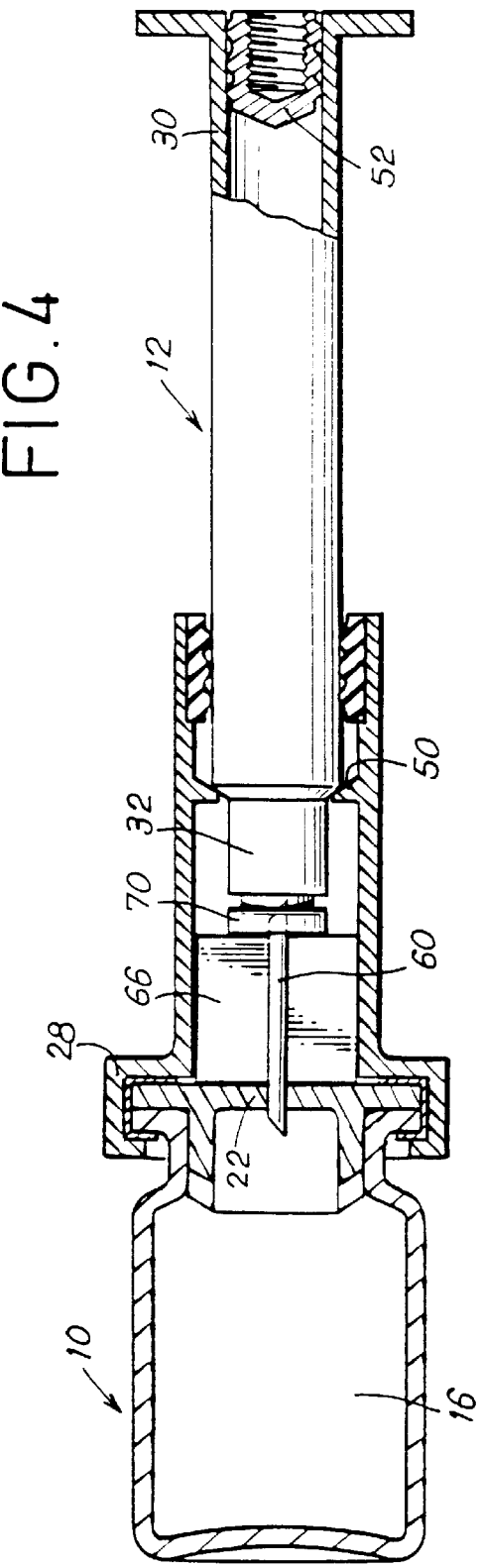

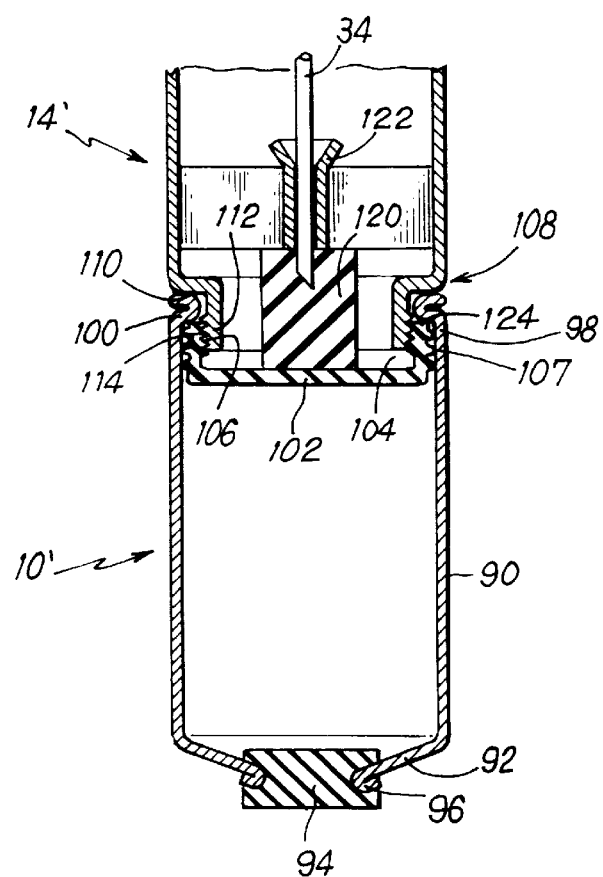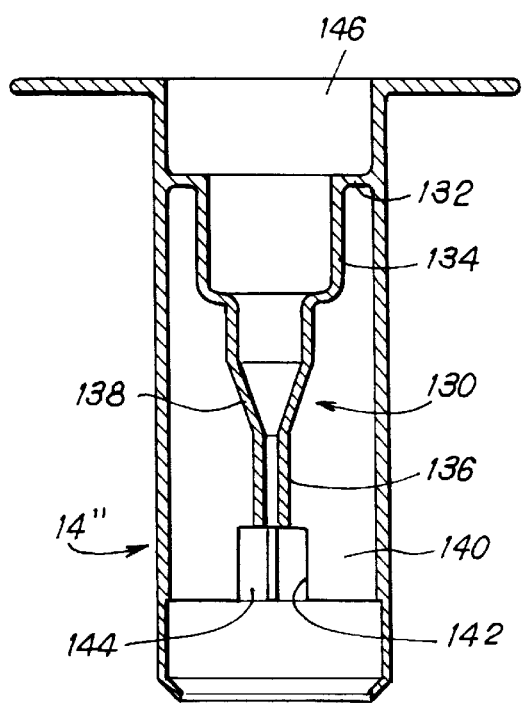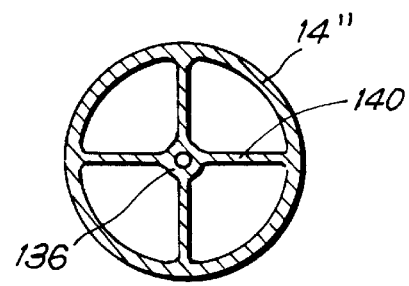

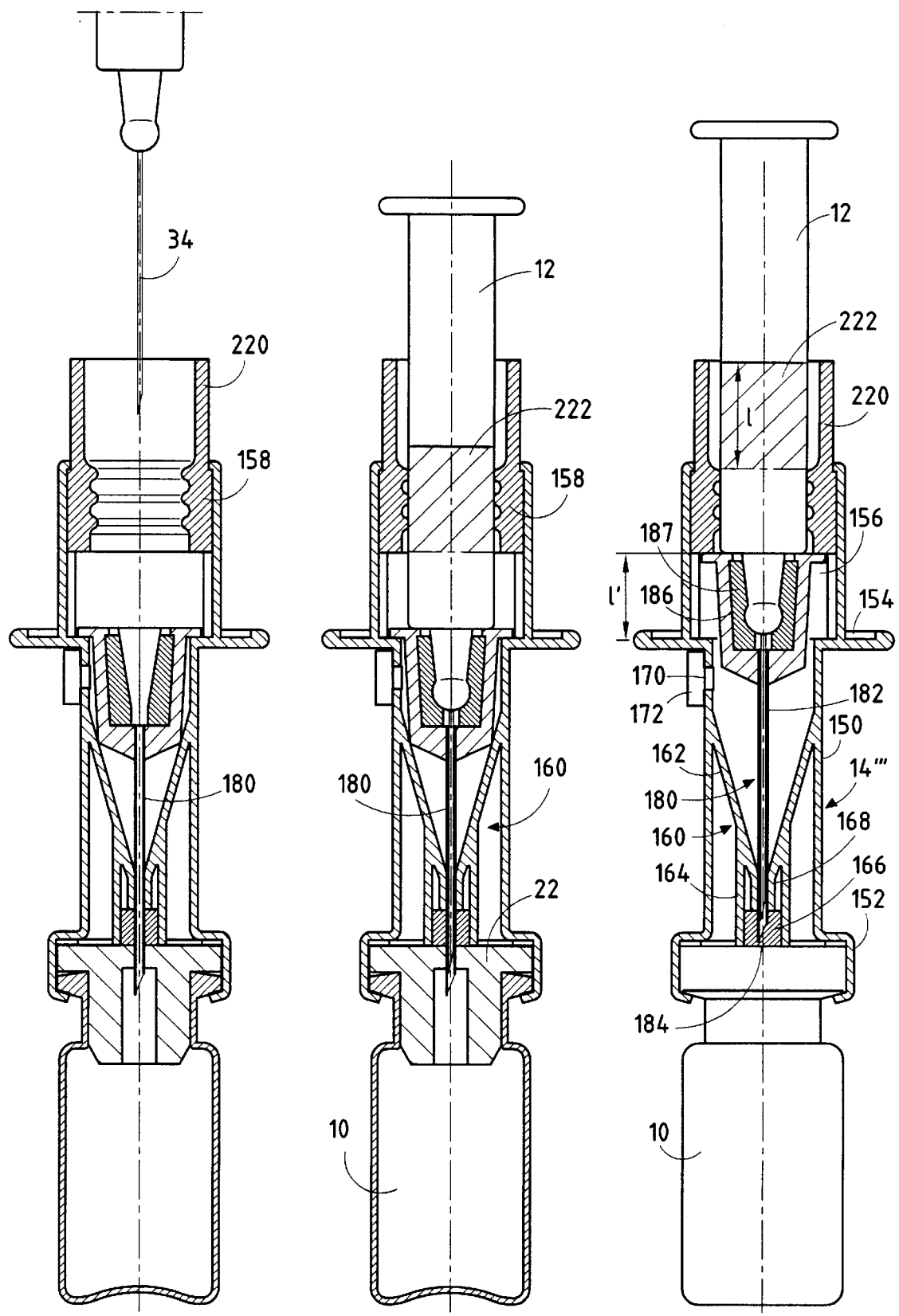

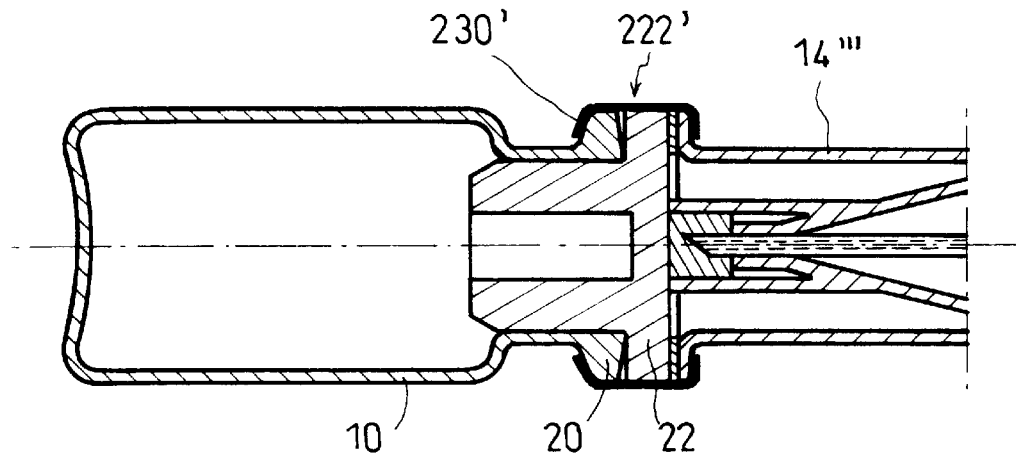
FIG_9c
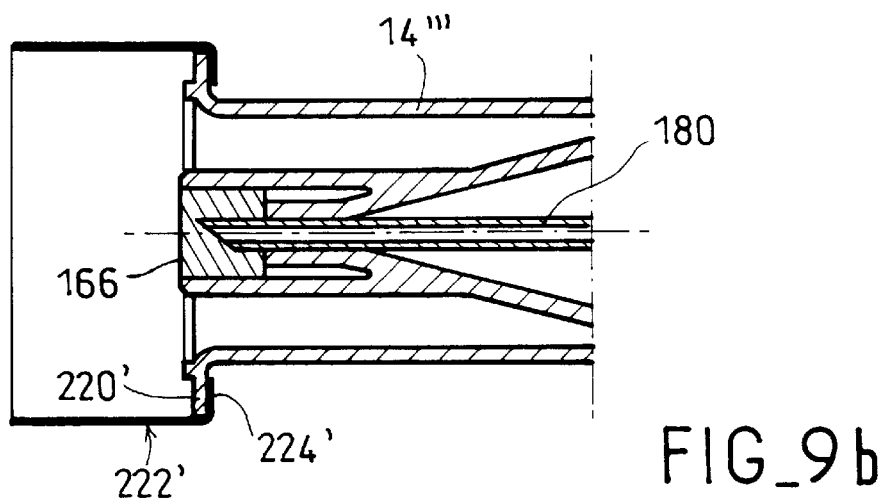
FIG_9b
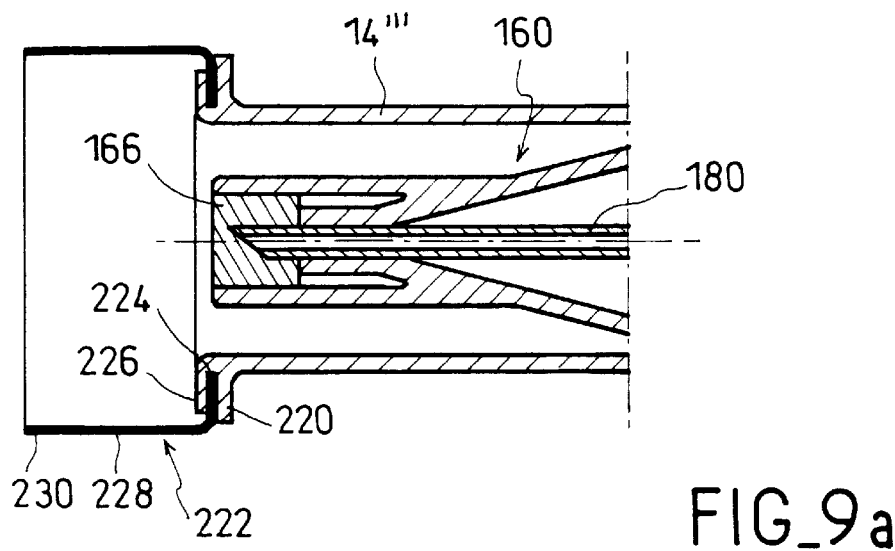
FIG_9a

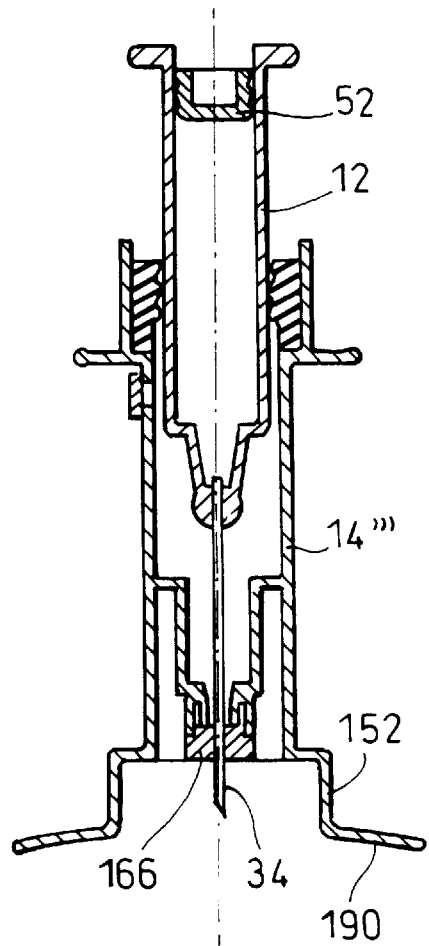
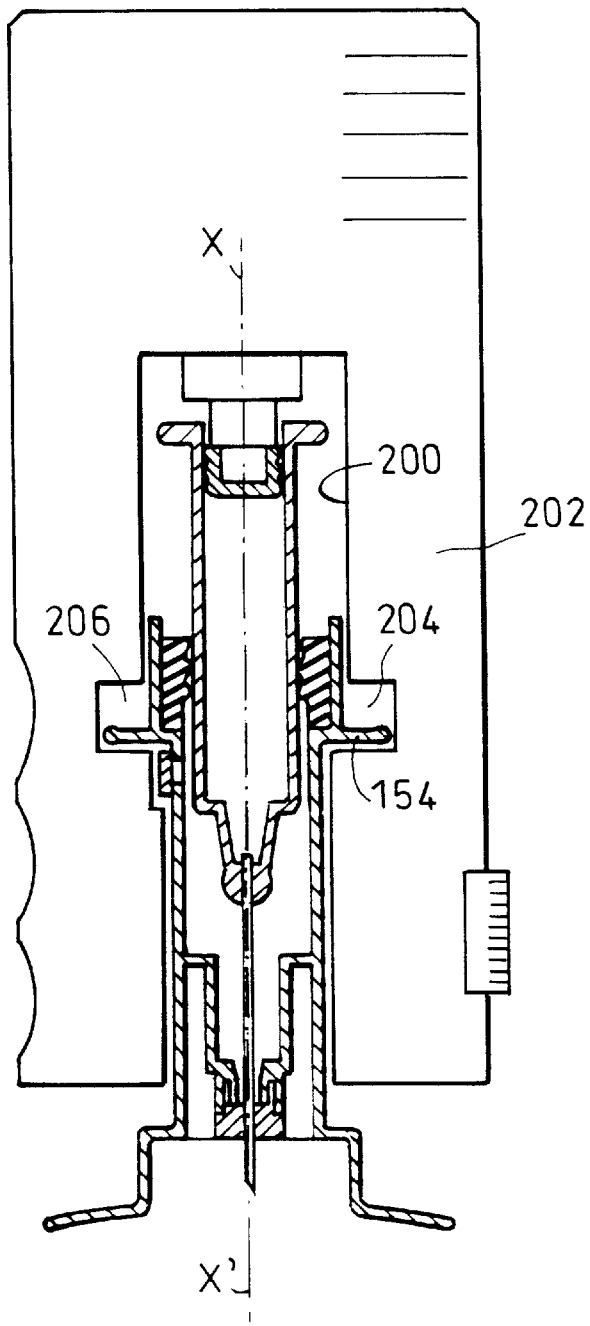
FIG_10a  FIG_10b

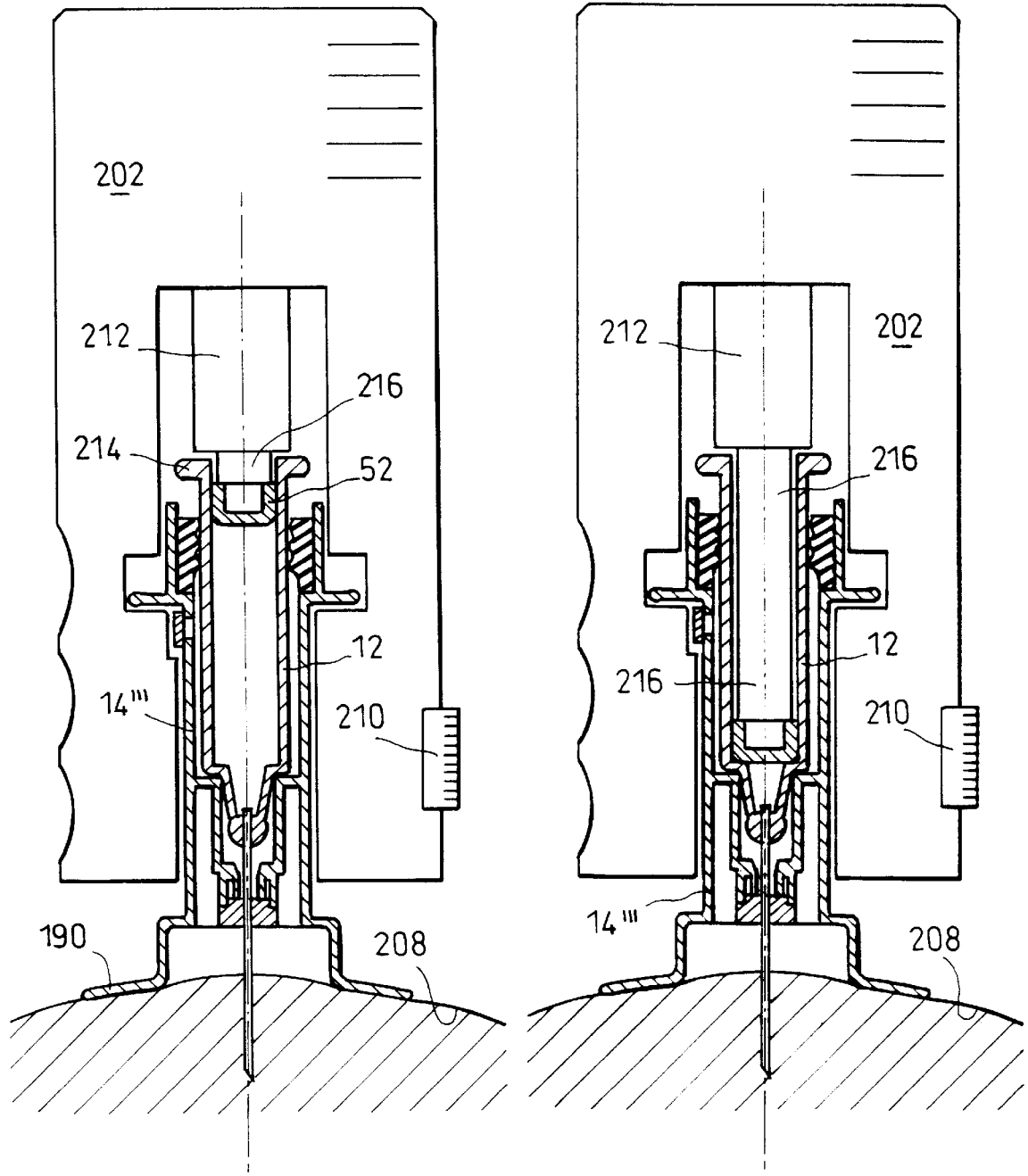
FIG_10c  FIG_10d

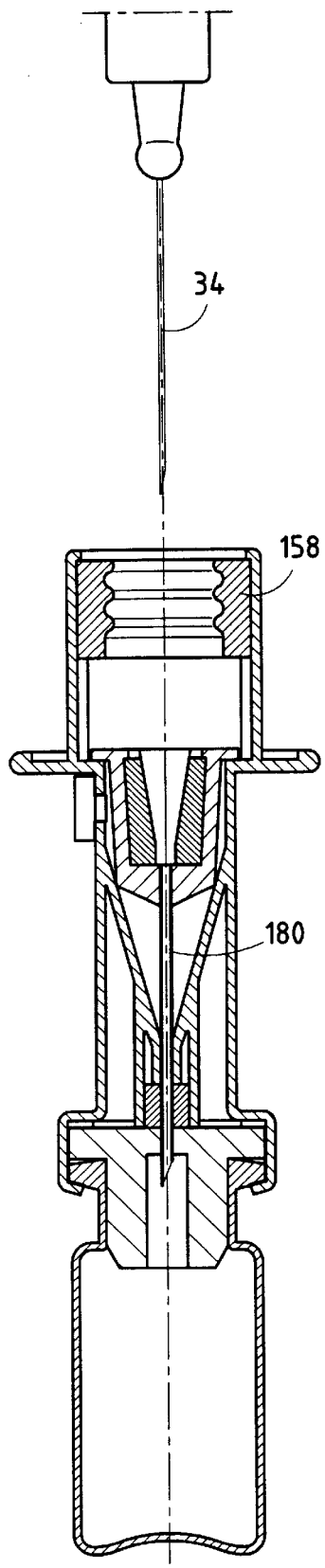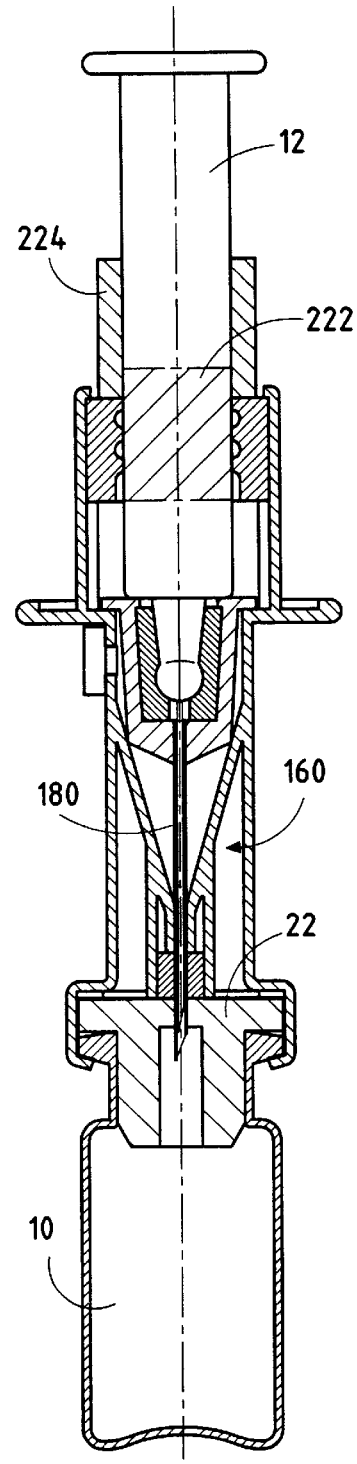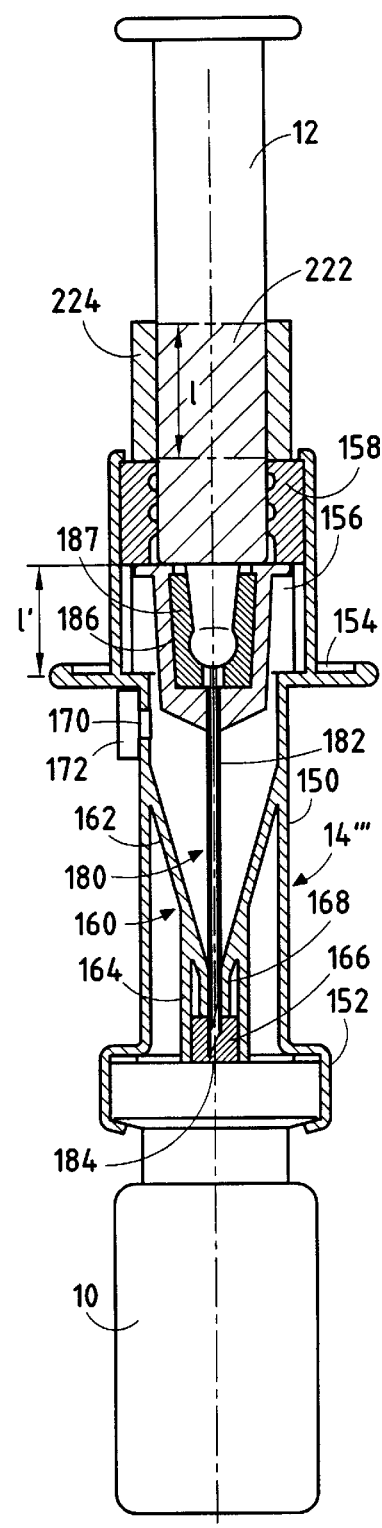

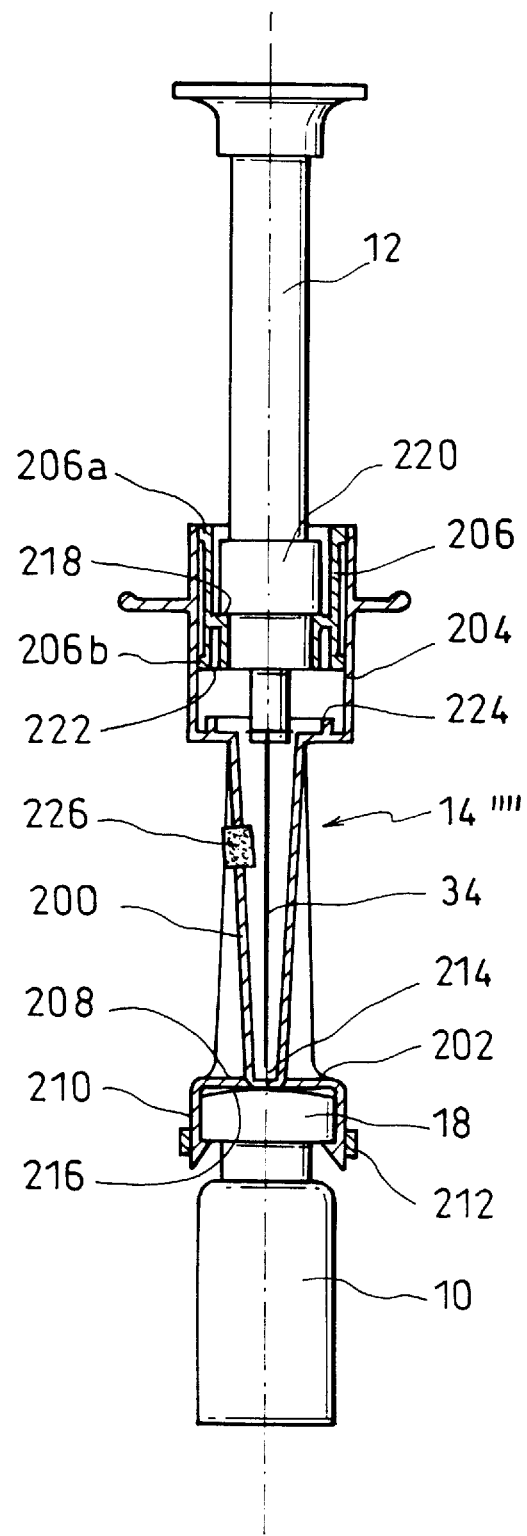
FIG_12

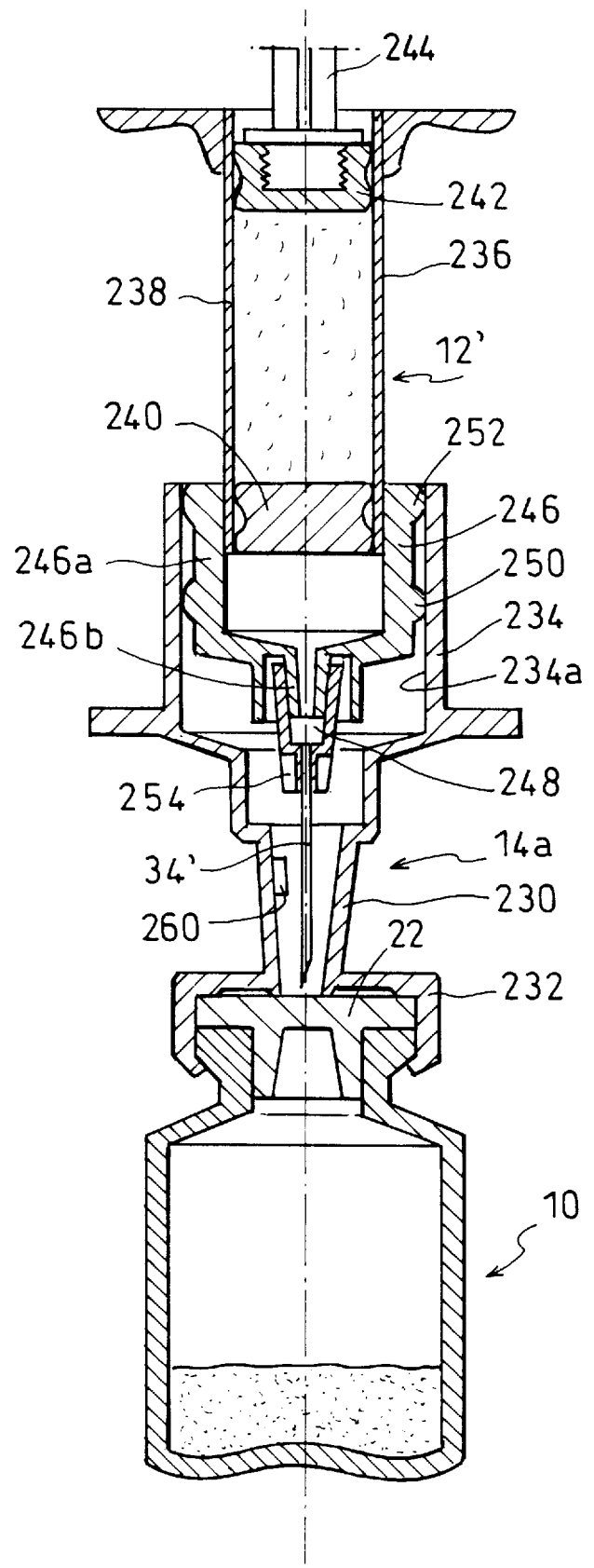
FIG_13

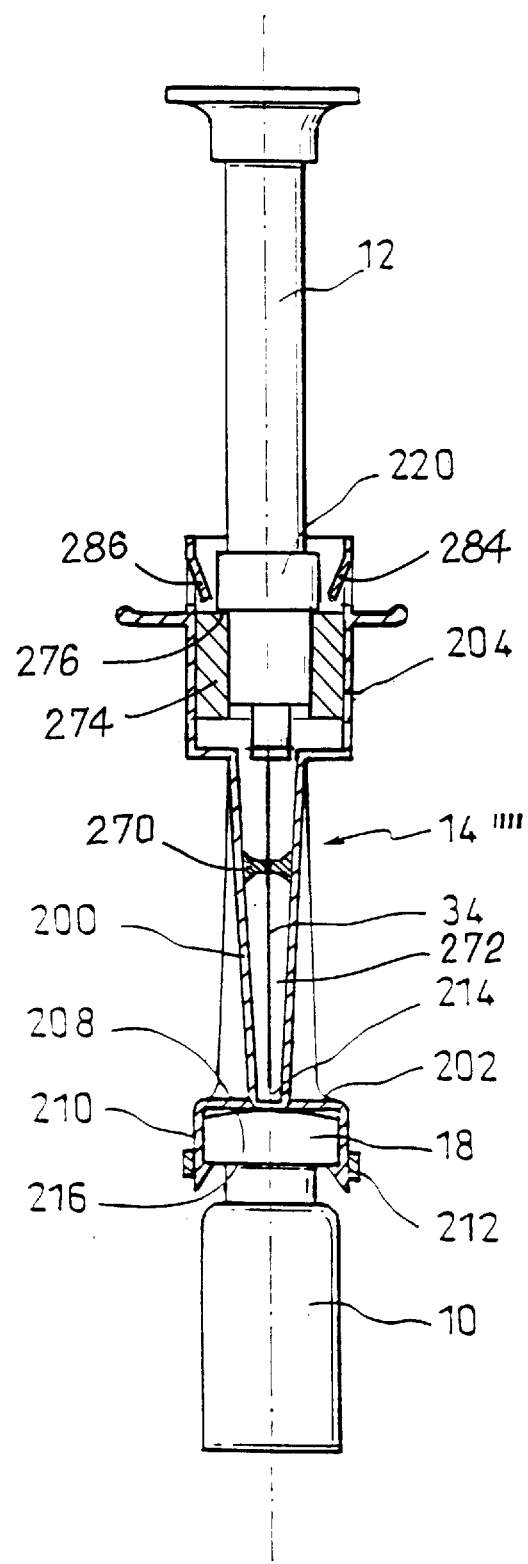
FIG_14a

SYRINGE DEVICE FOR MIXING TWO COMPOUNDS

The subject of the present invention is a syringe device making it possible to mix two compounds and inject the mixture thus obtained.

More precisely, the invention relates to a device allowing storage in separate form of two compounds which are to be mixed before they are injected.

It is known that there are, especially in the medical field, products which are to be stored separately and which must not be mixed until the time at which they are injected into a patient, for example subcutaneously, intravenously or intramuscularly. This is, in particular, the case of medicinal products which are prepared in freeze-dried form or in powder form, and which must be mixed with a solvent, for example physiological saline solution in order to allow them to be administered to the patient.

In other cases, the two compounds to be mixed may be liquids, it not being possible for these liquids to be preserved for a long time in mixed form.

The solution most frequently used consists in storing the powder in a separate container which is closed by a leaktight membrane which can be perforated using a needle. Furthermore, using a syringe, a certain quantity of solvent is withdrawn from a second container and injected into the first container through the membrane. The whole is then mixed in the first container and the mixture is sucked out using the same syringe. The syringe is then ready for carrying out the injection of the medication using, in most cases, a change of needle.

The solution described hereinabove has numerous drawbacks: on the one hand, it requires the use of the container closed by the perforable membrane, of the syringe and of the second container containing the solvent, which are separate articles. Furthermore, the handling operations required are relatively complex. On the other hand, it is not always easy to adhere to aseptic conditions during the various handling operations of the two components.

It is also necessary to consider the fact that freeze-drying installations preferably receive glass containers of standard form with a flat external bottom. It is therefore advantageous for the part of the syringe device intended to receive the product to be freeze-dried to have this form. In addition, most current medications are already in this form and any alteration of the packaging would require a new authorization to market, with long and expensive stability studies.

Furthermore, it is essential to ensure confinement of the needle throughout the storage period and preferably, during the handling operations corresponding to mixing the products.

One object of the present invention is to provide a syringe device making it possible to store the two compounds in separate enclosures, to mix these compounds and to inject them into a patient while preferably allowing freeze-drying of one of the two compounds in a first compartment independently of the sterilization of the solvent in a second compartment under conditions which are as close as possible to those which are encountered during freeze-drying of a product in a standard vial, the syringe device being in the overall form of a single assembly which is easy to handle and ensures, throughout its period of storage, maintenance of perfect asepsis of the various parts of the device which can come into contact with the patient or the product to be injected, and making it possible to carry out the handling operations for mixing the two products while keeping the needle under rigorous aseptic conditions.

In order to achieve this object, the syringe device making it possible to mix two compounds, at least the first of which is liquid, comprising a syringe provided with an injection end, the syringe containing the said first compound, is characterized in that it furthermore comprises:

means for guiding the injection end of the said syringe in translation between a first withdrawn so-called storage position and a second inserted so-called active position, the said guide means including a first end emerging opposite the perforable zone of a stopper capable of closing in leaktight manner the opening of a vial intended to contain one of the said compounds and a second end for receiving the injection end of the said syringe, the said second end comprising sealing means including a seal mounted inside the said guide piece and interacting with the external face of the syringe, and means for providing sufficient linkage between the said syringe and the said guide means while allowing the said translation; and communication means for allowing perforation of the said central region and communication of the internal volume of the said syringe with the inside of the said vial when the injection end of the said syringe is brought into its second position.

Preferably, the said vial forms an integral part of the syringe device. However, the scope of the invention will not be departed from if the syringe with its guide piece was provided independently from the vial, with both assemblies being linked subsequently.

Also preferably, the first sealing means provide a dynamic sealing between the guide means and the syringe body during all the relative displacements of these two pieces.

Preferably, the said first end of the guide means comprises means of linkage onto the opening of the said vial.

It will be understood that, by virtue of the arrangements of the invention, a single assembly is provided which includes, on the one hand, the vial containing the product, preferably freeze-dried and, on the other hand, the syringe which contains the solvent. However, the two are joined together by guide means which facilitate the mixing operation. Furthermore, it will be understood that the vial is a vial of the standard type used during conventional freeze-drying operations, since the guide means can be fitted only after the freeze-drying. Furthermore, by virtue of the sealing means, the needle is protected during storage against risks of contamination.

According to a first embodiment, the communication means comprise a needle mounted at the injection end of the syringe and whose tip is capable of perforating the central zone of the stopper when the end of the syringe is brought into its second position.

It will thus be understood that the needle fulfils the double role of allowing communication between the inside of the body of the syringe and the vial and that of a conventional injection needle once the syringe has been separated from the vial.

Also preferably, the syringe device includes a needle protector which surrounds the needle over its entire length and which has a perforating end extending beyond the tip of the needle and which is removable with respect to the said needle, by which perforation of the stopper of the vial is carried out via the first end of the needle protector.

According to a second embodiment of the invention, the communication means comprise a tubular piece arranged between the central zone of the stopper and the injection end of the syringe, the said tubular piece having a first end capable of closing the central zone of the stopper and a second end capable of piercing a perforable partition made at the injection end of the syringe when the latter is brought into its second position.

It will be understood that, in this second embodiment, the tubular piece includes two perforating ends which perforate the stopper of the vial and the perforable partition of the syringe when the syringe is inserted into the guide means, thus making it possible to mix the two compounds, the perforable partition is preferably itself a perforable stopper which closes the said syringe.

The same is true when a carpule equipped with a perforable stopper is arranged inside the syringe.

Also preferably, the guide means furthermore include second sealing means capable of providing, with the first sealing means, confinement of the communication means inside the said guide means.

Also preferably, the guide means include, between their first and their second ends, an orifice closed by an aseptic micropore filter.

The presence of this filter has a twofold advantage. On the one hand, it allows a part of the air contained in the guide means to leave, which greatly facilitates replacement of the syringe in the guide means whilst maintaining rigorous aseptic conditions during storage, inside the guide means. On the other hand, it makes it possible to carry out, through this filter, introduction of an asepticizing gas after fastening of the guide means on the vial.

Also preferably, the syringe device comprises an automatic injector device which is mounted on the syringe/guide piece assembly after this assembly has been detached from the vial. The automatic injector device comprises a support, means of translational immobilization of the said guide piece, first pusher means which can cause insertion of the syringe into the said guide piece by a first predetermined distance and second pusher means for causing insertion of the plunger of the syringe into the body of the syringe by a second predetermined distance, while not altering the position of the body of the syringe, the said first end of the guide piece forming a surface for bearing on the body of the patient.

It will be understood that the action of the first pusher makes it possible to insert the needle into the body of the patient by a predetermined distance, while the action of the second pusher makes it possible to carry out injection of the mixture.

Also preferably, the syringe device furthermore comprises annular protection means surrounding a part of the body of the said syringe in order to prevent manual access to the external face of the said part of the syringe body, a first end of the said protection means being adjacent to the said first sealing means when the said syringe occupies its first position in the said guide means, the axial length 1 of the protection means between its first end and its second end being at least equal to the travel 1' of the said syringe in the said guide means between its first position and its second position.

According to another embodiment, the seal comprises temporary means of linkage in translation with the body of the said syringe when the said syringe is displaced between its first and second positions. In this case the sealing lips are external and interact with the guide piece.

According to another embodiment, the first sealing means form an integral part of the syringe body. Also preferably, the syringe body consists of a carpule, at the end of which a plastic adapter carrying the needle of the syringe is fixed. The adapter has, on its external surface, at least one annular rib interacting with the internal face of the guide means for producing dynamic sealing.

According to yet another aspect of the invention, the guide means are preferably provided with a chamber for confining the gases which may leave the vial when the needle is extracted therefrom.

Other characteristics and advantages of the present invention will better emerge on reading the description which follows of several embodiments of the invention, given by way of non-limiting examples. The description refers to the attached figures, in which:

FIG. 1 is a view in longitudinal section of a first embodiment of the syringe device in its storage position;

FIG. 2 is a view similar to that in FIG. 1, showing the syringe device in a position allowing mixing of the compounds;

FIG. 3 is a view in longitudinal section of a second embodiment of the syringe device, this being in its storage position;

FIG. 4 is a view similar to that in FIG. 3 showing the syringe device in the position of mixing the compounds;

FIG. 6 is a partial view in longitudinal section of a fourth embodiment of the syringe device, including a vial of modified type;

FIGS. 7a and 7b represent another alternative embodiment of the guide piece, respectively in vertical section and in section along the plane BB of FIG. 7a;

FIGS. 8a and 8c show another alternative embodiment of the syringe device;

FIGS. 9a and 9b show two alternative embodiments of a guide piece provided with a crimping capsule;

FIG. 9c shows a syringe device including a guide piece according to FIG. 9b;

Figures 10a to 10d illustrate the use of an automatic injector device in conjunction with the syringe device;

Figures 11a to 11c are similar to FIGS. 8a to 8c, but show an alternative embodiment;

FIG. 12 shows, in vertical section, another embodiment of the syringe device;

FIG. 13 shows, in vertical section, another embodiment of the syringe device, illustrating another embodiment of the sealing means between the syringe body and the guide piece;

FIG. 14a shows a variant of the embodiment of the syringe device according to FIG. 12;

FIG. 18b is a partial view in vertical section showing the seal of FIG. 18a.

Figure 5:
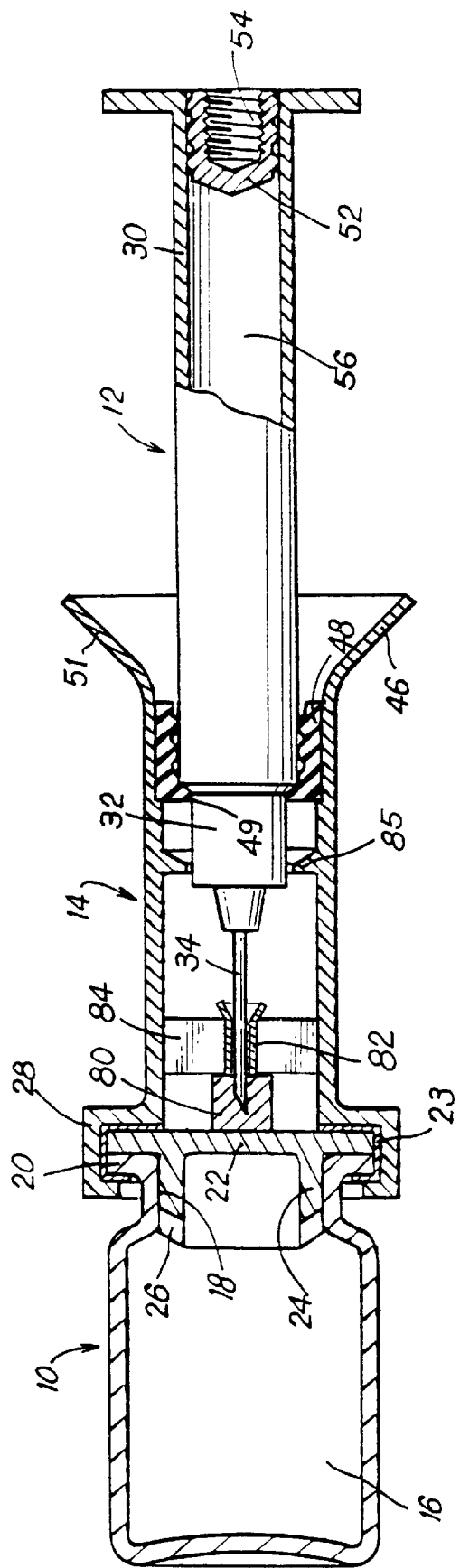
FIG. 5 is a view in longitudinal section of a third embodiment of the syringe device.

Referring first to FIG. 1, a description will be given of a first embodiment of the syringe device. The latter is essentially composed of a vial 10, of a syringe 12 and of a guide sleeve 14 mounted on the vial 10. More precisely, the vial 10 which is intended to hold a first compound to be mixed, labelled 16, which is preferably a freeze-dried compound, has an opening 18 which preferably ends in a collar 20. A stopper 22 of standard type closes the opening 18. This stopper is made of a perforable material and one which can be solidly linked in leaktight manner to the collar 20 of the vial by means of an aluminium capsule 23 which leaves the central part of the stopper free, this part being perforable.

Preferably, the stopper 22 includes a cylindrical body 24 which interacts with the opening 18 of the vial. This cylindrical body 24 includes axial openings 26, such that, when the stopper is partly engaged in the opening of the vial, the passages 24 allow circulation of gases during the freeze-drying operation, whereas, when the stopper is completely inserted, it produces perfect sealing.

The guide piece 14 preferably has, in this embodiment, a cylindrical form and includes a first end provided with a flange 28 for clipping onto the stopper 22 and the collar 20 of the vial thus ensuring linkage, at least in translation, between the guide piece 14 and the vial. The guide piece has a diameter slightly greater than that of the body 30 of the syringe 12. As is well known, the body of the syringe 30 terminates in an injection end 32 on which a needle 34 is mounted.

In the embodiment represented in FIG. 1, the needle is protected by a cap 36 whose end 38 interacts in leaktight manner with the injection end 32 of the syringe and whose second end 40 is perforable and is extended by a cylindrical washer 42 which interacts with an annular groove 44 made in the fastening flange 28 of the guide piece 14. The end 40 of the protective cap 36 is thus immobilized in translation and pressed flat against the perforable part 22 of the stopper of the vial 10. Furthermore, the washer 42, having its periphery clamped between the periphery of the stopper of the vial and the groove 44, covers the perforable part of the stopper in leaktight manner and ensures sealing of this end of the guide piece 14. As will be explained below, other modes of protection of the needle can be used. The open end 46 of the guide piece 14 is provided with an internal seal 48 which is calibrated so that it produces sealing between the guide piece 14 and the body 30 of the syringe, allowing translational displacement of the syringe inside the guide piece 14 whilst maintaining sealing throughout the translation. In order to produce this sealing, the elastic seal is preferably in ring form and preferably has three sealing lips 49' on its internal face. Furthermore, the length 1 of the ring along the direction of displacement of the syringe is sufficient to ensure sufficient linkage between the syringe and the guide piece 14 while allowing translational displacement of the syringe with respect to the guide piece under the effect of a force applied to the syringe. The length 1, is for example, equal to 1 cm. In addition, the length of the seal aids maintaining of the guide piece and of the body of the syringe in coaxial positions during the translational displacement of the latter. Preferably, the seal 48 defines a first retractable internal shoulder 49 which limits the insertion of the syringe into the guide piece when the syringe device is stored.

As also shown by FIG. 1, a second shoulder 50 is preferably provided inside the guide piece 14, which shoulder limits the possibility of insertion of the syringe 12 into the guide piece 14. The shoulder 50 is defined such that, when the end of the syringe comes to abut thereon, the end of the needle 34 has passed through the central part 22 of the stopper but projects only very slightly into the vial 10 in order to limit, as greatly as possible, the volume lost in the vial when it is desired to recover by suction, in the vertical position and with the aid of the needle, the mixture produced in the vial. Finally, as is well known, the syringe 12 includes a plunger 52 mounted sliding in the body of the syringe. This plunger 52 includes an internal screw thread 54 in which the control rod of the plunger 52 is fixed. In its storage position, the second compound to be mixed is arranged inside the volume 56 of the body of the syringe 12.

According to an alternative embodiment, the open end 46 of the guide piece 14 is extended by a flared frustoconical collar 51. The purpose of this collar is to protect the fingers of the operator who holds the guide piece during replacement of the syringe in this piece after injection into the patient. It is self-evident that the collar might be replaced by another form projecting out of the external face of the guide piece and capable of protecting the fingers of the operator which are placed on the side opposite the end 46 into which the syringe is reintroduced after having been used.

According to another variant, the clip flange 28 of the guide piece extends around the entire circumference of the stopper 22 and ensures, by clamping, leaktight fastening of the periphery of the stopper 22 onto the collar 20 of the vial. This arrangement makes it possible to avoid fitting of the metallic carpule 23 represented in FIGS. 1 and 2.

It is also possible to provide for the stopper 22 and/or the bottom 40 of the cap 36 of the needle to be preperforated at the centre. This characteristic makes it possible to reduce the force which must be applied to the syringe body so that the end of the needle passes through the cap and the stopper. Furthermore, this arrangement makes it possible to reduce the quantity of particles released from the stopper when the needle passes through it. This prevents these particles from being injected with the mixture. In fact, clamping of the stopper in the opening 18 of the vial ensures prestressing of the material constituting the stopper. A stopper 22 and/or the bottom of the cap 36 which, once fitted, is/are leaktight whilst having a preperforation.

Also preferably, the guide piece 14 is made of a synthetic material, for example polypropylene, allowing it to be sterilized by conventional techniques such as autoclaving, gamma radiation, etc.

The first embodiment of the syringe device, represented in FIG. 1, is used as follows: in a first step, the compound to be freeze-dried is arranged in the vial 10 which is then free of the guide piece 14. The stopper 22 is placed in its semi-inserted position. When the freeze-drying operation is finished, the stopper 22 is completely inserted and the aluminium capsule 24 is fitted. The syringe 12 containing the second liquid compound which has previously been sterilized is then fitted independently, with its protective cap 36, into the guide piece 14, then this assembly is fixed onto the vial by interaction between the flange of the guide piece 14 and the collar 20 of the vial 10. The syringe device is then in its state represented in FIG. 1 and is stored in this position. As a variant, the syringe may be fitted into the guide piece first of all. The syringe is then filled with the liquid and it is closed off with the plunger 52. This assembly is sterilized then fixed onto the vial 10. This assembly is optionally carried out under a laminar-flow fume cover.

When it is desired to inject the mixture of the freeze-dried compound 16 with the liquid 56 contained in the syringe 12, the following procedure is adopted: the body of the syringe 12 is inserted into the guide piece 14 until the body of the syringe comes to abut on the shoulder 50. In this position, the cap 36, which is elastic, deforms and the sharp end of the needle 34 has perforated the bottom 40 of the cap 36 and the perforable part of the stopper 22 of the vial. This is represented in FIG. 2. The needle 36 thus allows the inside of the body of the syringe 12 to communicate with the inside of the vial 10. It is then sufficient to mount the control rod in the plunger 52 of the syringe and partially insert this plunger in order to pass a suitable quantity of the liquid 56 into the vial 10 in order to mix the compounds 16 and 56. When mixing has actually been obtained in the vial 10, the plunger 52 is withdrawn in order to suck the mixture into the body 30 of the syringe, which is placed vertically. The latter is then ready for use. It is then sufficient to extract the syringe 12 from the guide piece 14. It will be understood that, during this operation, the cap 36 of the needle 34 is held on the vial 10 by the guide piece 14. It is possible to provide for the needle which has been used to perforate the stopper and to carry out the mixing to be detachable from the body of the syringe. It may then optionally be replaced by another needle for carrying out injecting of the mixture.

Referring now to FIG. 3, a description will begin of a second embodiment of the syringe device. In this second embodiment, the vial 10 intended to hold the freeze-dried compound 16 and its stopper 22 are identical to those in FIG. 1. They will not be described again. The same is true of the guide piece 14 whose end 28 is fixed onto the vial 10. The difference consists in that the needle 34 is replaced by a tubular piece 60 which has two perforating ends 62 and 64, the piece 60 being mounted inside the guide piece 14 between the injection end 32 of the syringe 12 and the stopper 22 of the vial 10. This tubular piece 60 is held in the axial position of the guide piece 14 by radial fins 66 which interact with the internal wall of the guide piece 14. Furthermore, the injection end 32 of the syringe is provided with a perforable partition 70 which is then arranged facing the end 62 of the tubular piece 60.

As a variant, the tubular piece 60 might consist of a double needle, between which a filter of suitable nature is interposed. It may also be provided that, during extraction of the syringe out of the guide piece 14, both needles are held in place at the injection end of the syringe.

As a variant, it is possible to interpose a seal, for example an O-ring, between the clip part 28 of the guide piece and the fastening capsule 23.

To use the syringe device and mix the compounds respectively contained in the body of the syringe and in the vial 10, the body of the syringe is inserted into the guide piece 14 until the syringe body comes to abut on the shoulder 50. In this position, as is better shown in FIG. 4, the sharp ends 62 and 64 of the tubular piece 60 respectively perforate the perforable partition 70 of the syringe and the central part of the stopper 22 of the vial. It is also seen that, in this position, the end faces of the radial guide fins 66 act as an end stop between the stopper 22 of the vial and the perforable partition 70 of the syringe, effectively ensuring perforation of the partition 70 and of the stopper 22. In this position, it is also possible to expel a part of the liquid contained in the syringe 12 by acting on its plunger 52. Once the mixing has been carried out in the vial 10, it is sufficient to pull on the plunger 52 in order to suck the mixture into the vertically placed body of the syringe. This same type of handling operating can be carried out with a carpule prefilled with liquid or with a syringe equipped with a carpule.

In order to carry out the injection,. it is sufficient to extract the syringe 12 from the guide piece 14 and fit a suitable needle at the injection end 32 of the syringe.

As a variant, it may be provided that, in order to carry out the injection of the mixture, it is the vial which is separated from the guide piece 14, the latter remaining solidly linked with the end of the syringe. For this, it is sufficient to provide, for the flange 28 for fastening the guide piece on the vial, a cutout which allows the latter to be torn, either manually or by rotating the guide piece with respect to the vial.

In this case, in order to carry out injection of the mixture into the patient subcutaneously or intramuscularly, it is necessary to carry out additional insertion of the syringe into the guide piece so that the tip of the needle actually projects out of the lower face of the fastening flange, the latter being in contact with the skin of the patient. In order to control this insertion, it is advantageous to provide an additional shoulder inside the guide piece, the shoulder 50 being retractable under the effect of the insertion of the syringe.

FIG. 5 illustrates a third embodiment of the syringe device. According to this embodiment, the cap 36 of the needle is replaced by a preferably cylindrical perforable piece 80 which is fixed in the end of the guide piece 14, the tip of the needle 34 penetrating into the perforable piece 80. This perforable piece 80 may be preperforated, as may the bottom of the cap 36. In order to guide the needle during fitting of the syringe in the piece 14, a guide tube 82 is provided which is arranged along the axis of the piece 14 and which is solidly linked thereto by means of radial fins such as 84. In this figure, an additional internal shoulder 85 has also been represented, which makes it possible to limit the insertion of the syringe into the piece 14 when the injection is carried out, in the case when the vial has been detached from the guide piece 14, the syringe remaining engaged in the guide piece.

As a variant, it is possible to provide for the part of the guide piece 14 surrounding the perforable piece 80 to have a smaller diameter than the main part of the piece 14 so that the side face of the perforable piece 80 is pinched in leaktight manner in this constriction, thus ensuring sealing inside the guide piece 14 in addition to the seal 48. Furthermore, it will be understood that, with the perforable piece 80 being forcibly pressed flat against the part of the stopper 22 which the needle will perforate, this part of the stopper is protected against risk of contamination. Furthermore, the pressure thus applied onto the stopper 22 improves the quality of the piercing of the stopper.

It will be understood that these second and third embodiments may include all the variants described in conjunction with the first embodiment, and in particular the preperforation of the stopper of the vial, the protective collar of the guide piece, the fastening of the stopper on the vial using the clip flange and the presence of an internal shoulder in this piece such that, after insertion of the needle, the end of the latter is substantially in the plane of the internal face of the stopper.

FIG. 6 shows a fourth embodiment of the syringe device which differs from the preceding embodiments essentially by the construction of the vial 10 which has the reference 10' in this figure. The vial 10' includes a preferably cylindrical body 90 whose bottom 92 is closed by a perforable membrane 94 whose periphery includes a groove which interacts with a rim 96 of the bottom of the vial. The second end 98 of the vial is preferably also provided with a rim 100. This end 98 is closed by a stopper 102 made of a perforable or optionally preperforated material. The stopper 102 is forcibly engaged into the vial beyond the rim 100. The stopper 102 includes, in its upper face, a recess 104 which is, for example, cylindrical. The side wall of the recess 104 is provided with an internal screw thread 106 whose function will be explained below. Preferably, the external side face 107 of the stopper has three lips for sealing with the internal face of the body of the vial.

The guide piece 14, which has the reference 14' in this figure, is also modified with respect to the guide pieces represented in FIGS. 1 to 5. The connection end 108 of the guide piece has an external shoulder 110 and is extended by a skirt 112 of smaller diameter than the main part of the guide piece. This skirt 112 is provided, on its external face, with a screw thread 114 which can interact with the internal screw thread 106 of the stopper. Finally, as in the case of FIG. 5, the end of the needle is implanted in a perforable piece 120 whose upper end is integral with a guide tube 122 and whose lower end bears on the bottom of the stopper 102.

The mode of use of the syringe device according to FIG. 6 is as follows:

The vial 10' is subjected to the operations already described for freeze-drying the product which it contains. The guide piece 14', with its syringe 12 filled with the liquid, is then fixed onto the vial 10' by screwing the skirt 112 of the guide piece onto the internal face of the stopper 102 of the vial. The shoulder 110 of the guide piece comes to bear on the rim 100 of the vial, while the screwing tends to apply the upper free edge 124 of the stopper onto the internal face of this same rim. The guide piece is thus linked to the vial 10' and the stopper 102 is also immobilized in translation.

The syringe 12 is then inserted into the guide piece 14'. The tip of the needle 34 perforates the piece 120 and the stopper 102, thus setting the inside of the vial 10' in communication with the inside of the syringe 12. By displacing the plunger 52 of the syringe, the liquid which it contained is passed into the vial 10' and the liquid is mixed with the freeze-dried product.

It is then possible to unscrew the guide piece 14' with respect to the stopper 102 of the vial 10' which becomes self-contained. The mixture is thus contained in a vial which has one end provided with a perforable membrane 94 and whose other end is closed by a stopper 102 which may act as a plunger. For this, it is sufficient to screw a control rod onto the internal screw thread of the stopper 102.

In order to administer the mixture contained in the vial 10' to a patient, it is sufficient to mount a double-tipped needle on the perforable membrane 94 and progressively insert the stopper 102 into the vial, the stopper acting as a plunger.

Similarly, the vial 10' may be used as a liquid reservoir for a pump mounted on a tube connected to the vial via its perforable membrane. In this case, the stopper 102 will be inserted into the vial under the effect of suction of the liquid by the pump.

In this latter embodiment, it will be understood that the function of the screw threads 106 and 114 is, on the one hand, temporarily to link the stopper 102 to the body of the vial 10' in proximity to its opening 18, in order to immobilize the stopper 102 and thus allow perforation by the tip of the needle of the syringe and, on the other hand, to free the stopper 102 in translation after removal of the guide piece 14', so that this stopper can act as a plunger. It is self-evident that the scope of the present invention will not be departed from if the syringe device were to be provided with other means capable of fulfilling this twofold function. For example, the stopper 102 might be provided with an external ring bearing on the periphery of the opening of the vial 10', thus preventing insertion of the stopper into the vial. After removal of the guide piece 14', this ring would be broken in order to allow insertion of the stopper 102 which could then act in its capacity of a plunger.

It will also be understood that the embodiment of the vial described in conjunction with FIG. 6 may be combined with the embodiment in FIGS. 3 and 4, that is to say with the case where the needle proper is replaced by the tubular piece 60 having the perforating tips 62 and 64.

Referring now to FIGS. 7a and 7b, a description will be given of an alternative embodiment of the guide piece, which then has the reference 14". Inside the piece 14", a guide piece 130 is provided which forms an integral part of the piece 14" and comprises a collar 132 for connection to the piece 14", a cylindrical portion 134 intended to receive the end of the body of the syringe when the latter is completely inserted into the piece 14" and a needle guide portion 136 which is connected to the cylindrical portion 134 by a substantially conical portion 138. Radial fins 140, readily visible in FIG. 7b, centre the guide part 130. The fins 140 have, at their lower ends, cutouts 142 defining a free volume 144 intended to receive the perforable piece 80 into which the tip of the needle is inserted. The perforable piece 80 is solidly linked to the guide piece 130. Finally, above the collar 138, the zone 146 of the guide piece 14" is intended to receive the seal 48.

When the guide piece 14" is mounted on the vial, the perforable piece 80 is pinched between the stopper 22 of the vial and the lower end of the guide portion 136. The perforable piece therefore closes the lower end of the guide part 130 in leaktight manner and it protects against contamination the perforable central piece of the stopper 22. Furthermore, when the syringe is fitted into the guide piece 14", the seal 48 ensures sealing at the other end of the guide part 130. During storage of the syringe device, the needle of the syringe is therefore completely protected inside the guide part 130. This protection remains throughout all the operations of mixing the two products.

Preferably, the syringe is fitted into the guide piece and this assembly is fixed onto the vial. In the case of the embodiment in FIGS. 7a and 7b, the inside of the piece 130 is closed in leaktight manner when the syringe body interacts with the seal 48. The air contained in this closed volume can act against insertion of the syringe until it arrives in its storage position, in which the tip of the needle penetrates into the piece 80. In order to allow escape of air during this phase, temporary fitting of a second needle which passes entirely through the piece 80 and emerges inside the piece 130 may be provided. This second needle may subsequently be used for introducing a gaseous disinfection agent into the piece 130. The second needle is then removed before fastening the piece 14" onto the vial. With the perforable piece being a septum, the orifice created by introducing the needle recloses after the latter is withdrawn.

Referring now to FIGS. 8a to 8c, a description will be given of a new alternative embodiment of the syringe device. According to this embodiment, the vial 10 and the syringe 12 may be identical to the corresponding elements represented in FIGS. 1 and 2 or 5. They will therefore not be redescribed.

The guide piece 14'" includes a cylindrical body 150, one end 152 of which forms an adapter for clip fastening on the neck 20 of the vial and the periphery of the stopper 22. At its second end, the cylindrical body is provided with a protective collar 154 and it is extended by a housing 156 intended to receive a seal 158, preferably a lip seal, which may be identical to that in FIG. 1. As already explained, this seal 158 ensures sealing between the body of the syringe 12 and the guide piece 14"40 during all the relative movements of the syringe with respect to the guide piece.

Inside the cylindrical body 150 there is a guide structure 160 which comprises a frustoconical portion 162 solidly linked to the body 150 and extended by a terminal cylindrical portion 164. In the terminal part 164 a perforable piece 166 is mounted which is made of an elastic material. Inside the cylindrical portion 164, a sleeve 168 solidly linked to the portion 166 is provided. The free end of the sleeve bears on the face 166a of the perforable piece 166. In addition, the second face 166b of the piece 166 projects slightly with respect to the free end of the cylindrical portion 164. Thus, when the guide piece 14'" is fixed on the vial 10, the perforable piece 166 is slightly compressed, which ensures pressure contact between the face 166b of the piece 166 and the central part of the stopper 22 which is intended to be perforated. This arrangement may also be provided for the perforable piece 80 or 120 in the embodiments of FIGS. 5 to 7.

FIG. 8a shows that the cylindrical body of the guide piece includes an orifice 170 arranged above the zone of connection of the guide structure 160 to the cylindrical body 150. The orifice 170 is closed by a micropore filter 172, of type known per se. The hydrophobic filter 172 has pores of very small size, capable of maintaining sterility of the volume bounded by the guide structure 160. For example, the pores of the filter have sizes of the order of 0.22 microns.

The filter 172 has a twofold function. On the one hand, it allows air to escape when the syringe 12 is inserted into the guide piece. This arrangement is extremely desirable because of the presence of the seal 158. On the other hand, it makes it possible, after fitting of the syringe in the guide piece 14''' and fastening of the latter on the vial, to introduce an aseptisizing gas into the guide structure. It is self-evident that a micropore filter similar to the filter 172 of FIGS. 8 might be mounted on the guide pieces 14 of FIGS. 1 to 5 or 14' and 14'' of FIGS. 6 and 7.

FIG. 8a also shows that the needle 34 of the syringe is preferably equipped with a needle protector 180. The needle protector 180 comprises a cylindrical sheath 182 which surrounds the needle 34. Its first end 184 is perforating and projects slightly beyond the tip of the needle. The other end of the sheath 182 comprises a removable piece 186 for fastening on the injection end of the body of the syringe 12. During fitting of the syringe in the guide piece 14''40, the end 184 of the needle protector 182 is guided by the sleeve 168 of the guide structure. In its final storage position, the tip 184 of the needle protector partially perforates the piece 166.

Preferably, the fastening piece 186 includes a part 187 made of elastic material which provides sealing between the end of the syringe carrying the needle and the needle protector 180.

In order to mix the products, as already explained, the syringe is inserted into the guide piece (FIG. 8b). During this displacement, it is the tip 184 of the needle protector 182 which perforates the piece 166 and the stopper 22 of the vial 10, thus protecting the tip of the needle 34. By virtue of the material of which it is constituted, the needle protector 182 remains wedged by friction in the stopper 22 and the piece 166 (FIG. 8c) when the syringe 12 is removed from the guide piece 14'''. The holding of the needle protector 182 may also result from the friction between the fastening piece 186 of the needle protector and the guide piece 14''', or alternatively from a particular form given to the latter which clips it onto the guide piece.

In the embodiments previously described, the guide piece is fastened on the vial by virtue of a particular form of the end 28 of the guide piece. FIGS. 9a to 9c illustrate another fastening mode.

According to the embodiment in FIG. 9a, the end of the guide piece 14''' consists of a circular collar 220 intended to come to bear on the periphery of the stopper 22 of the vial. A crimping capsule 222 in ring form includes a first curved-back part 224 which is engaged in a slot 26 of the collar 220 and a second cylindrical part 228. The free edge 230 of the cylindrical part 228 is intended to be crimped onto the lower face of the neck 20 of the vial in order solidly to link the guide piece 14''' on the vial.

FIG. 9b illustrates a variant of mounting the crimping capsule 222'. This includes a folded portion 224' which rests on the collar 220' forming the first end of the guide piece 14'''. The rest of the crimping capsule 222' is identical to the capsule 222.

FIG. 9c shows the fastening of the guide piece 14''' of FIG. 9b on the vial 10 provided with its stopper 22. The stopper 22 may already be fixed on the neck of the vial by a first fastening capsule, as shown in FIG. 1, or this stopper may alternatively be simply inserted into the opening of the vial. In both cases, the guide piece 14''' into which the syringe has already been fitted, is applied against the vial so that the collar 220' bears against the periphery of the stopper 22. The free edge 230' of the crimping capsule is then crimped.

It will be understood that the solution illustrated by FIGS. 9a and 9c makes it possible to simplify the linking of the vial 10 and of the piece and of the guide piece 14''' since the crimping capsule 222 or 222' is already fitted on the guide piece. It is self-evident that this mode of linkage can be applied to the embodiment described previously by modifying the form of the first end of the guide piece.

Referring to FIGS. 10a to 10d, a description will now be given for use of a syringe device with an automatic injector. The syringe device is of the type represented in FIGS. 8a to 8c, apart from the fact that it has no needle protector. Furthermore, the clip end 152 of the guide piece 14''' is preferably extended by a collar 190 forming a bearing surface, as will be explained below.

After the two products have been mixed and the mixture has been sucked into the syringe, as explained previously, the guide piece 14''' is detached from the vial 10 and the plunger 52 of the syringe 12 has its control rod removed. The syringe device is then in the state represented in FIG. 10a.

In the following step, represented in FIG. 10b, the syringe device is fitted in the cavity 200 of an automatic injector 202. The syringe 12 is arranged along the axis XX' of the cavity of the automatic injector and the syringe device is immobilized in translation, for example by interaction of the collar 154 with recesses 204 and 206.

FIG. 10c shows that the assembly thus prepared is positioned on the patient to be injected with the mixture. More precisely, the zone 190 is placed in contact with the part 208 of the body of the patient where the injection is to be carried out. By acting on the control button 210, a first pusher 212, which projects into the cavity 200 and which bears on the open end 214 of the body of the syringe, is caused to move out. Displacing the pusher 212 causes the syringe to be inserted into the guide piece 14''' and the needle 34 therefore to be inserted into the body of the patient by a predetermined length. During this operation, the plunger 52 of the syringe is not displaced with respect to the body of the syringe.

In the final operational phase represented in FIG. 10d, actuation of a second pusher 216, coaxial with the pusher 212, is caused with the pusher 212 remaining immobile. Displacing the pusher 216 leads to insertion of the plunger 52 of the syringe at a controlled rate until all of the mixture contained in the body of the syringe has been injected into the patient. Preferably, actuation of the control button 210 causes successive operation of the pusher 212 and of the pusher 216.

It will be understood that, when the operator manipulates the syringe device with a view to inserting the syringe into the guide tube for perforating the stopper of the vial, the external face of the syringe body, which is outside the seal of the guide tube risks being contaminated, especially by the hands of the operator. Now, a part of this surface, which is hatched in FIG. 8a, will penetrate into the leaktight and sterile chamber defined by the guide tube and the seal. This risks causing to contamination of this chamber and of the parts of the device which it contains.

FIGS. 8a to 8c illustrate a first embodiment of these protective means. They consist of a cylindrical skirt 220 which extends beyond the external end of the seal 158. The internal diameter of this skirt is greater than the external diameter of the body of the syringe. The axial length 1 of the skirt is at least equal to the travel 1' of the syringe in the guide tube 14''' between its storage position (FIG. 8*a*) and its perforation position (FIG. 8*b*). It will thus be understood that the hatched zone 222 of the external surface of the syringe, which is intended to penetrate into the tube, cannot be touched by the operator, which avoids the risks of contamination by contact of this zone.

FIGS. 11*a* to 11*c* illustrate a second embodiment of the annular protective means. These means consist of an elastic sleeve 224 which is mounted on the portion of the syringe body adjacent to the end of the seal 158 when the syringe is mounted in the guide tube. The hatched zone is therefore protected against any risk of contamination by contact or by surrounding air. The sleeve 224 has a length 1 which is at least equal to the travel 1' of the travel of the syringe body in the guide tube. When the syringe is inserted into the tube, the seal constitutes an end stop for the protective sleeve 22', the latter sliding with respect to the syringe body.

It is self-evident that the annular protective means which have just been described in conjunction with FIGS. 8 and 11 could be used with the embodiments described with reference to FIGS. 1 to 7 and 9.

FIG. 12 illustrates another embodiment of the syringe device, which makes it possible to protect the assembly against risks of contamination linked with the user gripping the syringe body. The guide piece 14''' includes a main part 200 of frustoconical shape, an end 202 for fastening on the vial 10 and a linking end 204 for receiving a seal 206 and the syringe body 12. The fastening end comprises a collar 208 and members 210 for clipping on the opening of the vial. The clip tabs may be supplemented by a crimping ring 212. Once fitted, the ring 212 can penetrate into a groove made in the clip tabs, thus locking the guide piece on the vial. The collar 208 leaves a central zone 214 free for passage of the needle 34. Preferably, the passage 34 is surrounded by a circular rib 216 which projects below the collar 208. This rib interacts with the stopper of the vial 10 to provide sealing between the two pieces.

The upper end 204 of the guide piece has a widened cylindrical form in which the annular seal 206 is mounted. This seal may be made of (butyl) rubber or of plastic. The seal 206 has a shoulder 218 which interacts in leaktight manner with a widened portion 220 of the syringe body. The seal 206 has, on its external face, two sealing rims 206*a* and 206*b* which provide dynamic sealing while allowing sliding of the seal under the effect of a thrust. On its lower edge, the seal preferably includes an annular recess 222 which interacts with a clip rib 224 when the syringe is completely inserted into the guide piece.

It will be understood that the inside of the guide piece containing the needle 34 is leaktight, especially with regard to contaminating germs, because of the seal 206 and of the sealing rib 216. Furthermore, the central zone of the stopper which will be perforated by the needle is also protected with respect to risks of contamination.

The mode of use of the syringe device of FIG. 12 is as follows: in the storage position represented in FIG. 12, the seal 206 is in a position not inserted into the guide piece. When the mixing of the product contained in the vial 10 with the liquid contained in the syringe is to be carried out, the syringe is inserted into the guide piece 14'''', which causes simultaneous insertion of the seal 206 by virtue of the interaction of the shoulder 218 and of the part 220 of the syringe body. At the end of insertion of the syringe, the clip elements 222 and 224 interact and solidly link the seal on the guide piece. After having filled the syringe with the mixture, it is sufficient to extract this syringe from the seal which remains solidly linked to the guide piece.

It is important to observe that, by virtue of the displacement of the seal 206 caused by the insertion of the syringe, the part of the syringe outside the guide piece in the storage position, which can be contaminated by the user, remains external to the leaktight zone internal to the guide piece, bounded by the position of the seal 206. There is therefore no risk of contamination of the needle in the insertion phase.

It may be advantageous to equip the main part of the guide piece with an orifice obstructed by a bacteriological filter, the whole being labelled by the reference 226. This filter allows air to leave when the syringe is being inserted into the guide piece, while maintaining asepsis of the space containing the needle 34.

However, since the seal 206 is a sliding seal and is held in the inserted position after extraction of the syringe, the overpressure when the syringe is reintroduced is greatly reduced. The filter is therefore less indispensable for this function.

A plurality of alternative embodiments may be provided within the scope of the invention. In particular, it is possible to provide for the needle to detach, during withdrawal of the syringe with respect to the guide piece, from the end of the syringe while remaining implanted, for example, in the perforable piece or in the cap.

According to an alternative embodiment, the form of the seal between the guide piece and the syringe body may be modified in order to facilitate separation of the syringe with respect to the guide piece. For this, a screw thread is made in the external face of the seal, this screw thread interacting with an internal screw thread made in the internal face of the guide piece. The internal face of the seal remains provided with its sealing lips. In order to separate the syringe from the guide piece, it is sufficient to rotate the body of the syringe, which leads to unscrewing of the seal. Of course, other means might be used for removable linkage of the seal on the end of the guide piece.

FIG. 13 illustrates another embodiment of the syringe device, showing in particular another way of producing sealing between the syringe body and the guide piece.

The syringe body includes a vial 10 intended to receive a product, especially the freeze-dried product, and closed by a perforable stopper 22. A guide piece having the reference 14*a* is fixed on the vial. This guide piece includes a frustoconical portion 230 extended by a collar 232 for fastening on the stopper and on the neck of the vial 10. At the other end of the frustoconical portion 230, a cylindrical portion 234 is provided which is actually used for guiding the syringe which in this case has the reference 12'. In this particular embodiment, the syringe 12' consists of a carpule 236 formed in the conventional manner by a cylindrical glass body 238 which is closed at its first end by a stopper 240 and at its second end by another stopper forming a plunger 242. The plunger 242 can receive the end of the control rod of the syringe 244. At the first end of the carpule 238, a cylindrical adapter 246 is fixed which is solidly linked to the end of the carpule. The adapter 246 includes a cylindrical part 246*a* and a frustoconical end 246*b* in which the fastening end 248 of a needle 34' is screwed. As shown by FIG. 13, the cylindrical part 246*a* of the adapter 246 is provided, on its external surface, with two annular ribs 250 and 252 forming sealing lips, these ribs projecting out of the external wall of the adapter and interacting with the internal face 234*a* of the cylindrical part of the guide piece. It will be understood that the two ribs or lips 250 and 252 form a dynamic seal between the adapter 246 and therefore the syringe 12' and the part 234 of the guide piece 14a. This sealing is maintained during the insertion phase of the syringe 12' for perforating the stopper 22 of the vial 10. It will be understood that the ribs 250 and 252 thus constitute, in this embodiment, the first means of sealing between the syringe body 12' and the guide piece 14a.

Preferably, the head 248 of the needle 34' includes radial ribs such as 254. Inside the frustoconical part 230 of the guide piece, a portion 260 is provided which forms a projection into the guide piece. This portion 260 comes level with the ribs 254 of the needle 34' when the latter has been inserted in order to perforate the stopper 22. It will be understood that, in order to detach the needle 34' from the adapter 246 in complete safety, it is sufficient for the user to rotate the syringe 12' when it is in the inserted position. Since the projecting element 260 is interposed between the ribs 254 of the head of the needle, the rotational movement causes automatic unscrewing of the needle without the user having to touch it.

It will thus be understood that it would not depart from the invention if the syringe body 12' were to consist of a syringe of conventional type made of a slightly deformable plastic. In this case, the annular sealing ribs 250 and 252 would be made directly on the external face of the syringe body. The automatic means for unscrewing the needle might similarly be provided in this case.

FIG. 14a illustrates an alternative embodiment of the syringe in FIG. 12. In this embodiment, the guide piece 200 is provided with a perforable leaktight elastic membrane 270 which defines a leaktight volume 272 with the perforable stopper of the vial 10. In the storage position, the needle 34 passes in leaktight manner through the membrane 270. The membrane 270 is used for confining in the volume 272 the fraction of residual liquid or of gas which might leave the vial 10 when the tip of the needle 34 is withdrawn out of the vial because of the temporary and local deformation of the perforable stopper in the perforation region and the overpressure possibly existing in the vial after mixing. Due to its elasticity the perforation of the membrane is closed as soon as the needle is withdrawn out. This gas confinement chamber arrangement may be provided in all the embodiments of the syringe device.

FIG. 14a also shows a new embodiment of the seal for sealing between the upper part 204 of the guide piece and the syringe. The annular seal 274 includes an internal face clamped onto the syringe body 12 and interacts with a shoulder 276 of the syringe such that insertion of the syringe body also causes insertion of the seal. The upper part 206 of the guide piece includes two small retractable elastic tongues 284 and 286 which project into the guide piece. In the storage position represented in FIG. 14a, the tongues 284 and 286 project between the upper lip 282 and the intermediate lip 280. This therefore prevents the seal 274 from accidently leaving the guide piece or from being accidently inserted.

Figure 14B:
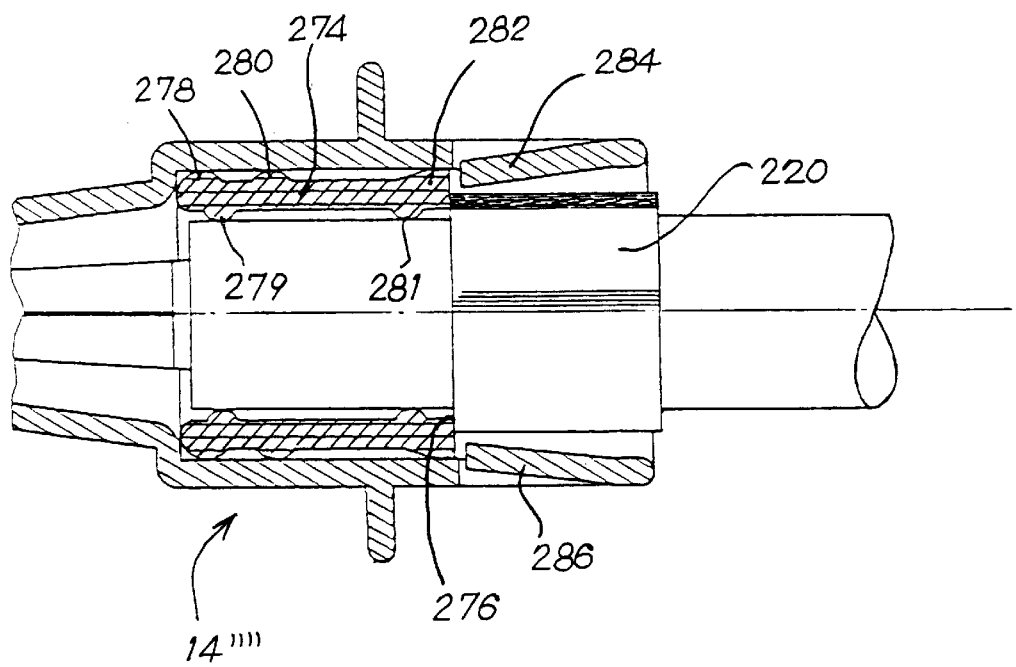
FIGS. 14b and 14c are detail views of FIG. 14a, showing the seal in the storage and use positions.
Figure 14C:
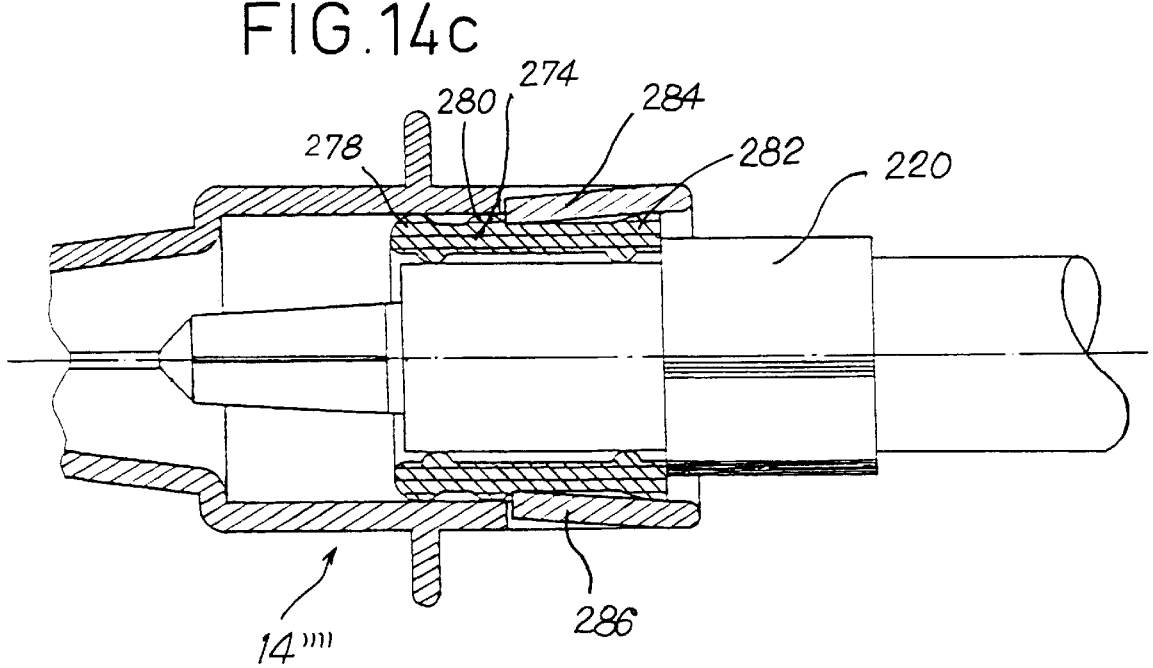

FIGS. 14b and 14c show the seal 274 and its mode of action in more detail. The seal preferably has three external sealing lips 278, 280 and 282 in contact with the internal face of the guide piece and two internal lips 279 and 281 in contact with the syringe body. In the storage position (FIG. 14a) the seal is in the upper position and the tongues are engaged between the upper lip 282 and the middle lip 280. The tongues 284 and 286 act as non-return end stops allowing the seal 274 to be inserted only and preventing it from leaving.

In this position, sealing is provided by the middle lip 280 and by the lower lip 278. Furthermore, the interaction of the tongues 284, 286 with the intermediate lip 280 prevents the seal 274 from leaving the guide piece accidently.

When the syringe is inserted in order to perforate the stopper of the vial, the seal 274 is moved along by the syringe body, and the upper lip 282 causes temporary deformation of the tongues such that the lip passes "below" the tongues. The tongues, by virtue of their non-return function, prevent displacement of the seal during extraction of the syringe out of the guide piece. The seal is held in the inserted position.

Figure 15:
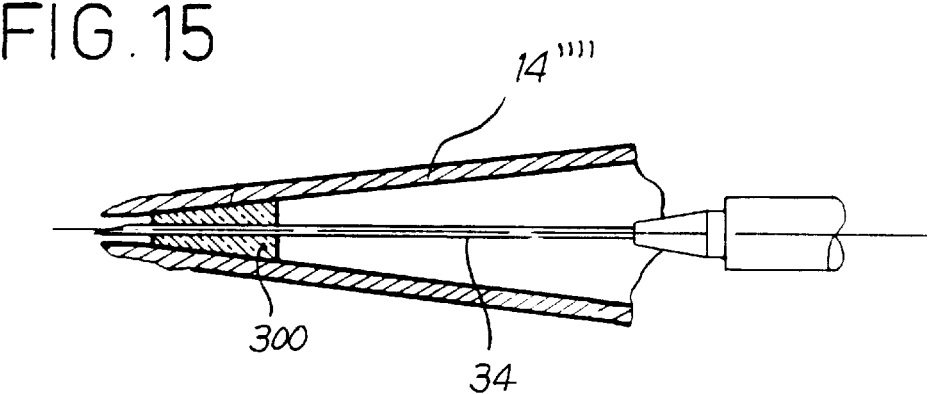
FIG. 15 illustrates a first alternative embodiment of the gas confinement chamber.

FIG. 15 illustrates another embodiment of the confinement of the noxcious gases capable of leaving the vial. It consists in arranging a piece 300 made of porous materials such as a porous foam at the end of the frustoconical part of the guide piece 14'''. When the needle is extracted from the vial, the gases possibly leaving the latter are absorbed, blocked or trapped by the piece 300. Of course, the piece 300 is passed through by the needle 34.

Figure 16A:
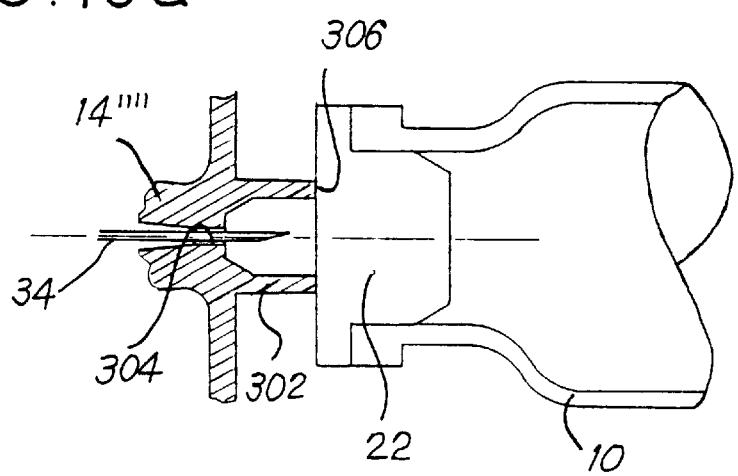
FIGS. 16a and 16b show two other alternative embodiments of the gas confinement chamber.
Figure 16B:
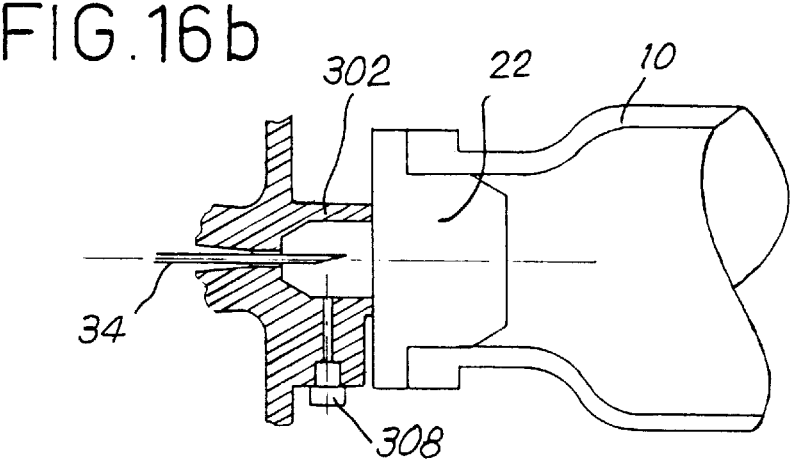

FIGS. 16a and 16b show two other embodiments of the confinement chamber for the gases. The lower end of the conical part of the guide piece is extended by a housing 302 connected to the guide piece by a passage 304 whose diameter is substantially equal to that of the needle 34. The wall of the housing 302 terminates in a free edge 306 which is applied in leaktight manner onto the stopper 22 of the vial. A substantially leaktight chamber is thus produced, in which the gases possibly leaving the vial are confined.

In the case when the mixture to be injected can produce a large quantity of gas, it is advantageous to provide the wall of the housing 302 with a micropore filter 308 which allows to balance the overpressure due to the filtered gases leaving the housing 302 whilst filtering the noxcious part of the gas.

Figure 17:
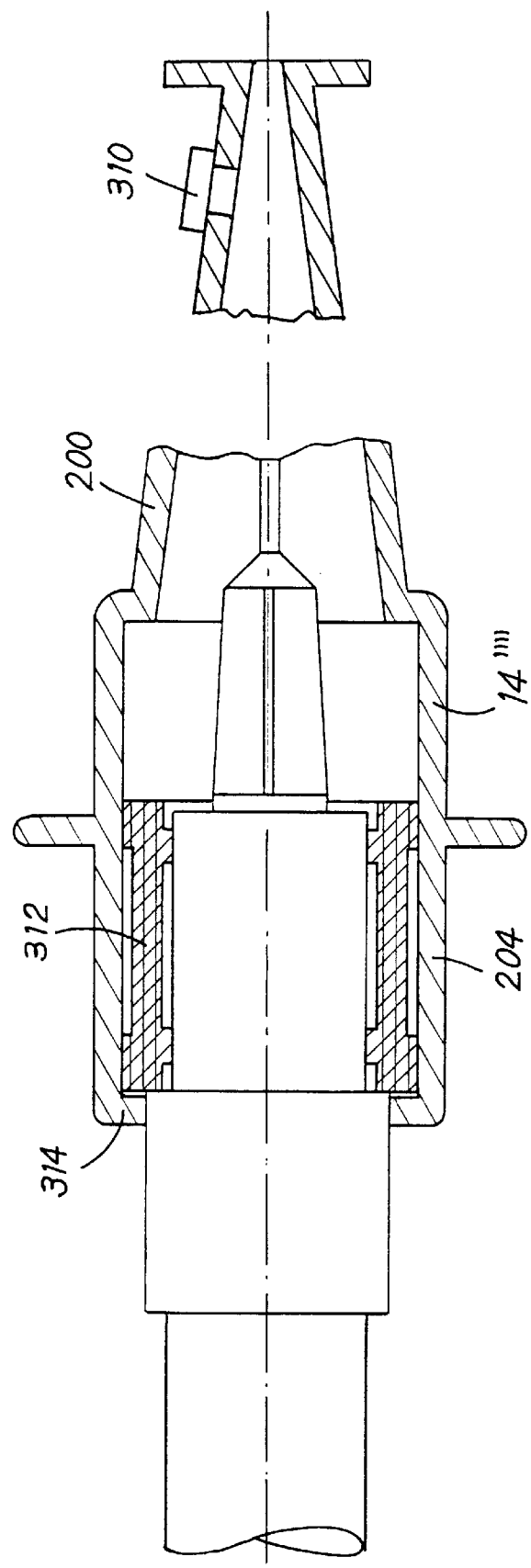
FIG. 17 illustrates an alternative embodiment of the syringe device allowing confinement of the gases.

FIG. 17 illustrates another mode of recovery of the gases which can leave the vial during extraction of the needle. The conical part 200 of the guide piece 14'''' is provided with a micropore filter 310 allowing controlled removal of the gas. In order to allow removal of the gas while maintaining sealing of the guide piece 14'''', the seal 312 which includes internal and external sealing lips between the syringe body and the guide piece is retained in the guide piece only by an upper shoulder 314 which prevents the leaving of the seal out of the guide piece, the side wall of the guide piece being itself leaktight. Thus, throughout the syringe extraction phase, the inside of the guide piece remains leaktight by interaction of the seal 312 and the syringe. The gas consequently has time to excape through the filter 310 in order to balance the gas overpressure within the guide piece whilst filtering the noxcious gas thanks to filter 310.

After mixing the products, the operator must extract the syringe from the guide piece. Because of the nature of the materials constituting the guide piece, the seal and the syringe, important friction forces may occur. As a result, the operator must exert a certain force on the syringe with respect to the guide piece in order to release the former. During said operation, it is possible that, by an untimely movement from the operator, the needle pricks the hand of the operator holding the guide piece. In order to avoid said risk and according to an improved embodiment of the syringe device, the extraction of the syringe is carried out in two motions. Firstly, the syringe is partially extracted from the guide piece with most of the resistant forces due in particular to friction being overcome. Secondly, after a particular handling operation, the syringe is completely released from the guide piece without no important traction forces being exerted by the user. In order to obtain this result, a mechanical end stop is provided which limits the extraction of the syringe during the first extraction step since the final extraction may only be obtained after rotation of the syringe with respect to the guide piece.

Figure 18A:
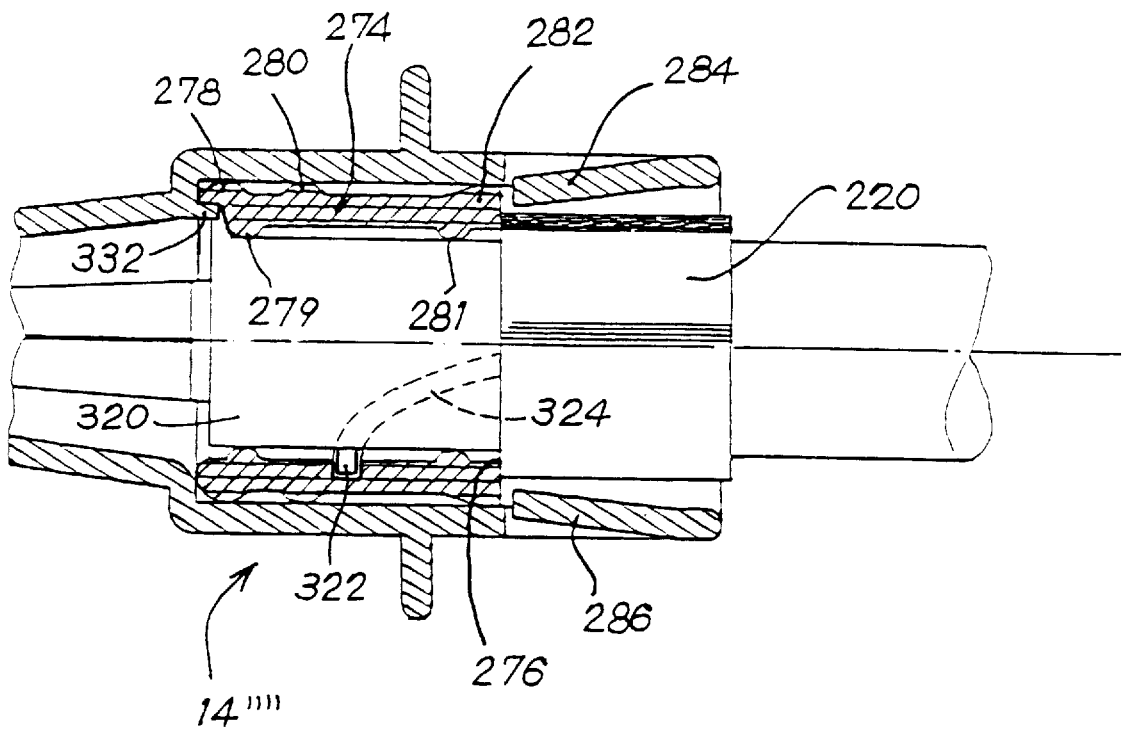
FIG. 18a shows a part of the syringe device in an embodiment making it possible to control the extraction of the syringe outside the guide piece.
Figure 18B:
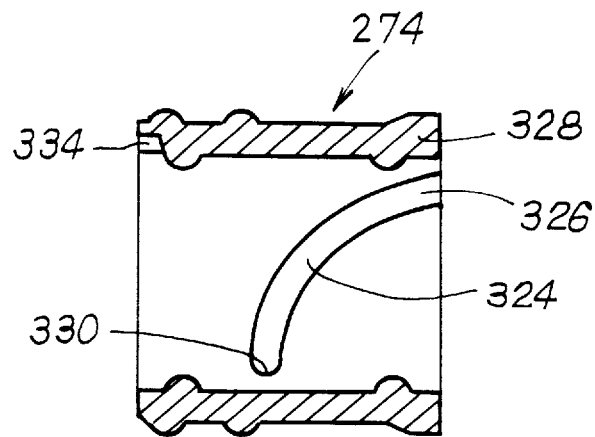

FIGS. 18a and 18b show this arrangement in the case of the embodiments of FIGS. 14. However, it is self-evident that said arrangement might be easily transposed to the other embodiments of the syringe device.

As shown in FIG. 18a, the end 320 of the syringe is provided with a snug 322. The snug 322 is engaged inside a helical notch 324 provided in the internal face of the seal 274. The end 326 of the notch 324 emerges inside the upper face 328 of the seal; however, its other end is blind. The notch 324 corresponds to a rotation of 90 degrees, for example. It will be understood that said internal notch does not break the sealing provided by the seal 274. Furthermore, a notch 322 projecting outside the guide piece interacts with a recess 334 of the seal by immobilizing it in rotation. In the storage position and during the mixing operation of the products, the notch 322 bears against the blind end 330 of the notch. When the user exerts a traction force on the syringe, the friction forces are released and the syringe remains solidly linked to the seal 274 and thus to the guide piece. It is only once the syringe has been rotated by 90 degrees with respect to the guide piece that the notch 322 is opposite the open end 326 of the notch and that the syringe can be completely extracted. Said extraction is carried out without any significant force being exerted and the operator's movement can be perfectly controlled.

Of course other solutions that merely allow the leaving of the syringe in two motions separated by a rotation operation of the syringe can be envisaged.

As already mentioned, the syringe device preferably comprises the syringe with its guide piece and the vial with its perforable stopper. However, the scope of the present invention will not be departed from by providing separately the syringe with its guide piece and the vial, both components being solidly linked subsequently so as to reconstitute a complete assembly. In this case, it is self-evident that, during the storage period, the first end of the guide piece must be closed in leaktight manner to insure the asepsis of the needle. Another solution might consist in sterilizing the guide piece and the end of the syringe with its needle immediately after mounting it on the vial.

The person skilled in the art will also understand that the first sealing means between the syringe and the guide piece might also consist in a seal mounted between these two elements and consisting in a sealing bellows mounted, on the one hand, on the syringe and, on the other hand, on the guide piece. The distortions of the bellows then absorb the relative displacements of the syringe and of the guide piece during the mixing operations.

We claim:

1. A syringe device making it possible to mix two compounds, at least the first of which is liquid, comprising:

a syringe provided with a body having an injection end, the syringe adapted to contain said first compound;

means for guiding the injection end of said syringe body in translation between a first withdrawn storage position and a second inserted active position, said guide means including an inner face, a first end emerging opposite the perforable zone of a stopper capable of closing in leaktight manner the opening of a vial intended to contain the other compound and a second end for receiving the injection end of said syringe, said second end comprising means for providing sufficient linkage between said syringe and said guide means while allowing said translation;

an annular seal surrounding said syringe body and secured to said syringe body and disposed between said body and said guide means and close to the second end of the guide means when the syringe is in its first position, said annular seal having an outer face provided with at least one sealing lip for cooperating with the inner face of the guide means; and communication means for allowing perforation of said stopper and communication of the internal volume of said syringe with the inside of said vial when the injection end of said syringe is brought into its second position.

2. Syringe device according to claim 1, wherein said linking means comprise a crimping capsule mounted on said first end of said guide means and capable of being crimped into a collar of the opening of said vial during the fastening of said guide means on said vial.

3. Syringe device according to claim 1, wherein said linking means comprise clip tabs interacting with the periphery of the opening of the vial.

4. Syringe device according to claim 3, wherein said clip means furthermore comprise a crimping ring interacting with the clip tabs.

5. Syringe device according to claim 1 wherein the communication means comprise a needle mounted at the injection end of the syringe and whose tip is capable of perforating the central zone of the stopper when the end of the syringe is brought into its second position.

6. Syringe device according to claim 1, wherein said stopper is preperforated.

7. Syringe device according to claim 1, wherein said first sealing means are capable of providing said sealing during the relative displacement of said syringe with respect to the guide means.

8. The syringe device according to claim 7, wherein said seal is made of elastomer.

9. The syringe device according to claim 7, wherein said seal is made of plastic.

10. Syringe device according to claim 1, wherein said seal has the form of a ring whose face which interacts with the body of the syringe includes at least two sealing lips.

11. Syringe device according to claim 1, wherein said seal comprises temporary means for translational linkage with the body of said syringe when said syringe is displaced between its first position and its second position.

12. The syringe device according to claim 11, wherein said temporary linkage means comprise a shoulder made on the face of the seal interacting with a relief of the body of the syringe, whereby said seal is moved along when the syringe body is inserted.

13. The syringe device according to claim 12, wherein said interaction means provide sealing between said seal and said syringe body.

14. The syringe device according to claim 11, wherein said seal includes a first locking element capable of interacting with a second locking element when said seal is in its second position.

15. The syringe device according to claim 11, wherein the face of said seal interacting with the guide piece includes at least two sealing lips.

16. Syringe device according to claim 1, wherein the first sealing means consist of a seal having the shape of an annular ring linked in translation with the syringe in the insertion direction, said ring having, on its external face, sealing lips interacting with the external face of the guide means and said guide piece has, in its external face, retractable tongues capable of interacting with said lips, whereby said seal is prevented from leaving said guide piece.

17. Syringe device according to claim 16, wherein said ring comprises three sealing lips and, in the storage position, said tongues are arranged between the outermost lip and the intermediate lip.

18. Syringe device according to claim 1, wherein the guide means furthermore include second sealing means capable of providing, with the first sealing means, confinement of the communication means inside said guide means.

19. Syringe device according to claim 18, wherein said second sealing means cover the portion of the stopper of said vial intended to be perforated by the communication means.

20. Syringe device according to claim 19, wherein said first end of the guide means includes a collar capable of bearing on the opening of said vial, and means of fastening on said vial, said collar including, in its face turned towards the vial, a projecting annular portion for interacting in leaktight manner with the stopper of said vial.

21. The syringe device according to claim 1, wherein said annular seal comprises a seal having the shape of an annular ring linked in translation with the syringe in the insertion direction, said ring having, on its external face, sealing lips interacting with the internal face of the guide means and with said guide means are provided, in its external face, retractable tongues capable of interacting with said lips, whereby said seal is prevented from leaving said guide means.

22. Syringe device according to claim 21, wherein said ring comprises three sealing lips and in the storage position, said tongues are arranged between the outermost lip and the intermediate lip.

23. The syringe device according to claim 1, wherein said annular seal comprises an annular ring linked in translation with the syringe in the insertion direction, said ring having, on its internal and external faces, sealing lips, and said guide piece includes shoulder means to prevent said seal from leaving said guide means.

24. A syringe device making it possible to mix two compounds, at least the first of which is liquid, comprising:
 a syringe provided with an injection end, the syringe adapted to contain said first compound;
 means for guiding the injection end of said syringe in translation between a first withdrawn storage position and a second inserted active position, said guide means including a first end emerging opposite the perforable zone of a stopper capable of closing in leaktight manner the opening of a vial intended to contain the other compound and a second end for receiving the injection end of said syringe, said second end comprising means for providing sufficient linkage between said syringe and said guide means while allowing said translation;
 an annular seal having an inner face sealingly facing the external face of the syringe body and an outer face provided with at least one sealing lip for cooperating with the inner face of said guide means, said annular seal being located close to the second end of the guide means when the syringe is in its first position, said syringe body being provided with a shoulder for moving said annular seal when said syringe body is moved from the first position to the second position; and
 communication means for allowing perforation of said stopper and communication of the internal volume of said syringe with the inside of said vial when the injection end of said syringe is brought into its second position.

25. The syringe device according to claim 1, wherein said annular seal comprises an annular ring linked in translation with the syringe in the insertion direction, said ring having, on its internal and external faces, sealing lips, and said guide piece includes a shoulder to prevent said seal from leaving said guide piece.

26. The syringe device according to claim 24, wherein said annular seal forms an integral part of the body of the syringe.

27. Syringe device according to claim 26, wherein the body of the syringe is made of plastic and said first sealing means consist of at least one annular lip projecting from the body of the syringe and interacting with the internal face of the guide means.

28. Syringe device according to claim 26, wherein the syringe consists of a carpule extended by a plastic adapter, at the end of which a needle is mounted, said adapter having, on its external face, at least one annular rib interacting with the internal face of the guide means, said rib constituting said first sealing means.

29. Syringe device according to claim 28, wherein said needle is screwed onto said adapter, the head of said needle being provided with radial ribs capable of interacting with a portion forming a projection into the guide piece, by which rotation of the syringe body allows unscrewing of said needle with respect to the adapter.

30. Syringe device according to claim 24, wherein said seal has the form of a ring whose face which cooperates with the body of the syringe includes at least two sealing lips.

31. Syringe device according to claim 24, wherein said seal is made of elastomer.

32. Syringe device according to claim 24, wherein said seal is made of plastic.

33. The syringe device according to claim 24, wherein said seal comprises temporary means for translational linking with the body of said syringe when said syringe is displaced between its first position and its second position.

34. Syringe device according to claim 33, wherein said temporary linking means comprise a shoulder made on the face of the seal interacting with a relief of the body of the syringe, by which said seal is moved along when the syringe body is inserted.

35. The syringe device according to claim 33, wherein said shoulder provides sealing between said seal and said syringe body.

36. The syringe device according to claim 33, wherein said seal includes a first locking element capable of interacting with a second locking element when said seal is in its second position.

37. The syringe device according to claim 33, wherein the face of said seal interacting with the guide means includes at least two sealing lips.

38. The syringe device according to claim 24, wherein the communication means comprise a needle mounted at the injection end of the syringe and whose tip is capable of perforating the central zone of the stopper when the end of the syringe is brought into its second position.

39. The syringe device according to claim 24, wherein said stopper is preperforated.

40. The syringe device according to claim 24, wherein said seal is capable of providing said sealing during the relative displacement of said syringe with respect to the guide means.

41. The syringe device according to claim 24, wherein said seal is made of elastomer.

42. The syringe device according to claim 24, wherein said seal is made of plastic.

43. The syringe device according to claim 24, wherein the guide means further includes second sealing means capable of providing, with the annular seal, confinement of the communication means inside said guide means.

44. The syringe device according to claim 43, wherein said second sealing means cover the portion of the stopper of said vial intended to be perforated by the communication means.

45. The syringe device according to claim 43, wherein said first end of the guide means includes a collar capable of bearing on the opening of said vial, and means of fastening on said vial, said collar including, in its face turned towards the vial, a projecting annular portion for interacting in leaktight manner with the stopper of said vial.

46. The syringe device according to claim 24, wherein said guide means internally comprise a perforable, elastic, leaktight membrane arranged between the first end and the second end of said guide means, said membrane being passed through, when the device is in its storage position, by said communication means, whereby the zone located between said membrane and said stoppers forms retention chamber making it possible to collect the gases which may leave said vial.

47. The syringe device according to claim 24, wherein said guide means further includes, between their first end and their second end, an orifice closed by a micropore filter.

48. The syringe device according to claim 24, wherein said guide means includes, in proximity to its first end, a piece made of porous material, passed through by said needle and capable of absorbing possible gases leaving said vial during the extraction of the needle therefrom.

49. The syringe, device according to claim 24, wherein said first end of the guide means is extended by a housing connected to the inside of the guide by a passage for passage of the needle, the free edge of said housing being applied against the stopper of said vial, whereby said housing forms a retention chamber for the gases which may leave said vial.

50. The syringe device according to claim 24, further comprising a control rod for a plunger of the syringe, said rod being screwable into said plunger.

51. The syringe device according to claim 24, further comprising an automatic injection device mountable on the assembly consisting of said syringe and said guide means after separation of said vial, said automatic injection device comprising a support for the guide means on said support, first pusher means for causing insertion of the body of the syringe with respect to said guide means by a first predetermined distance and second pusher means for causing insertion of said plunger with respect to the body of said syringe by a second predetermined distance, without altering the relative position of the syringe and of the guide means, said first end of the guide means forming a zone for bearing on the body of the patient.

52. The syringe device according to claim 24, comprising exit means for controlling the syringe outside said guide means including means for allowing the exit of the syringe from the guide means only in part such that the communication means remain in said guide means, and means allowing the complete exit of the syringe only once a rotation movement has been imparted to the syringe with respect to said guide means.

* * * * *